(12) United States Patent
Kim et al.

(10) Patent No.: US 10,441,441 B2
(45) Date of Patent: Oct. 15, 2019

(54) DRIVING MODULE, MOTION ASSISTANCE APPARATUS INCLUDING THE DRIVING MODULE, AND METHOD OF CONTROLLING THE MOTION ASSISTANCE APPARATUS

(71) Applicant: Samsung Electronics Co., Ltd., Suwon-Si, Gyeonggi-Do (KR)

(72) Inventors: Jeonghun Kim, Hwaseong-si (KR); Minhyung Lee, Anyang-si (KR); Hyun Do Choi, Yongin-si (KR); Se-gon Roh, Suwon-si (KR); Youn Baek Lee, Yongin-si (KR); Jongwon Lee, Uiwang-si (KR); Byungjune Choi, Gunpo-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1226 days.

(21) Appl. No.: 14/578,774

(22) Filed: Dec. 22, 2014

(65) Prior Publication Data
US 2016/0038313 A1 Feb. 11, 2016

(30) Foreign Application Priority Data
Aug. 7, 2014 (KR) .................. 10-2014-0101743

(51) Int. Cl.
*A61H 3/00* (2006.01)
*A61F 2/70* (2006.01)
(Continued)

(52) U.S. Cl.
CPC .............. *A61F 2/70* (2013.01); *A61F 5/0102* (2013.01); *A61H 1/0244* (2013.01); *A61H 3/00* (2013.01);
(Continued)

(58) Field of Classification Search
CPC ................... A61H 1/0244; A61H 3/00; A61H 2201/1207; A61H 2201/1238;
(Continued)

(56) References Cited

U.S. PATENT DOCUMENTS 5,062,824 A 11/1991 Prokopius
8,556,758 B1 10/2013 Schoenek et al.
(Continued)

FOREIGN PATENT DOCUMENTS

CN 103200909 A 7/2013
EP 1547568 A1 6/2005
(Continued)

OTHER PUBLICATIONS

European Extended Search Report dated Jan. 13, 2016 for corresponding EP Application No. 151/5306.8.
(Continued)

*Primary Examiner* — LaToya M Louis
(74) *Attorney, Agent, or Firm* — Harness, Dickey & Pierce, P.L.C.

(57) ABSTRACT

Driving modules, motion assistance apparatuses including at least one of the driving modules, and methods of controlling at least one of the motion assistance apparatus may be provided. For example, a driving module including a driving source on one side of a user and configured to transmit power, an input side rotary body connected to the driving source and configured to rotate, and a first decelerator and a second decelerator configured to operate using the power received from the driving source through the input side rotary body, wherein a gear ratio from the input side rotary body to an output terminal of the first decelerator differs from a gear ratio from the input side rotary body to an output terminal of the second decelerator, may be provided.

15 Claims, 37 Drawing Sheets

(51) Int. Cl.

| | | |
|---|---|---|
| *F16H 3/66* | (2006.01) | |
| *F16H 7/02* | (2006.01) | |
| *A61F 5/01* | (2006.01) | |
| *A61H 1/02* | (2006.01) | |
| *B25J 9/00* | (2006.01) | |
| *B25J 9/10* | (2006.01) | |
| *A61F 2/74* | (2006.01) | |
| *A61F 2/68* | (2006.01) | |

(52) U.S. Cl.
CPC ............. *B25J 9/0006* (2013.01); *B25J 9/102* (2013.01); *B25J 9/104* (2013.01); *F16H 3/66* (2013.01); *F16H 3/666* (2013.01); *F16H 7/02* (2013.01); *A61F 2002/6836* (2013.01); *A61F 2002/74* (2013.01); *A61H 2003/007* (2013.01); *A61H 2201/1207* (2013.01); *A61H 2201/1238* (2013.01); *A61H 2201/149* (2013.01); *A61H 2201/164* (2013.01); *A61H 2201/165* (2013.01); *A61H 2201/1628* (2013.01)

(58) Field of Classification Search
CPC ...... A61H 2201/149; A61H 2201/1628; A61H 2201/164; A61H 2201/165; A61H 2003/007; B25J 9/0006; F16H 3/66; F16H 3/663; F16H 3/666; F16H 3/70; F16H 7/02; F16H 9/23; F16H 2001/289
See application file for complete search history.

(56) References Cited

U.S. PATENT DOCUMENTS

| | | |
|---|---|---|
| 2005/0247511 A1 | 11/2005 | Kirkwood |
| 2005/0279558 A1 | 12/2005 | Kirkwood |
| 2006/0142105 A1 | 6/2006 | Kudoh et al. |
| 2008/0045374 A1* | 2/2008 | Weinberg ................ B25J 9/102 475/342 |
| 2010/0009799 A1 | 1/2010 | Ciszak et al. |
| 2010/0113210 A1* | 5/2010 | Lopez .................... F16H 1/2845 475/331 |
| 2010/0329868 A1* | 12/2010 | Ben ....................... F16H 57/082 416/170 R |
| 2011/0130242 A1 | 6/2011 | Gobel |
| 2011/0275477 A1* | 11/2011 | Hsieh ....................... F16H 1/46 475/331 |
| 2012/0077637 A1* | 3/2012 | Chen ....................... B25J 9/102 475/336 |
| 2013/0296746 A1 | 11/2013 | Herr et al. |
| 2013/0331744 A1 | 12/2013 | Kamon |
| 2015/0272809 A1 | 10/2015 | Accoto et al. |

FOREIGN PATENT DOCUMENTS

| | | |
|---|---|---|
| EP | 2055288 A1 | 5/2009 |
| EP | 2327617 A2 | 6/2011 |
| GB | 2214579 A | 9/1989 |
| JP | 55-20945 A | 2/1980 |
| JP | 2006-220272 A | 8/2006 |
| JP | 2009240488 A | 10/2009 |
| JP | 2014-030338 A | 2/2014 |
| JP | 2014-073199 A | 4/2014 |
| KR | 101146112 B1 | 5/2012 |
| KR | 1020130037766 A | 4/2013 |
| KR | 101304086 B1 | 9/2013 |
| KR | 101315199 B1 | 10/2013 |
| KR | 20130111763 A | 10/2013 |
| WO | WO-2014/057410 A1 | 4/2014 |

OTHER PUBLICATIONS

Chinese Office Action dated Jul. 3, 2018 issued in Chinese Application No. 201510166515.3 (English translation provided).

Japanese Office Action dated Jan. 8, 2019 issued in Japanese Application No. 2015-056768 (partial English translation provided).

* cited by examiner

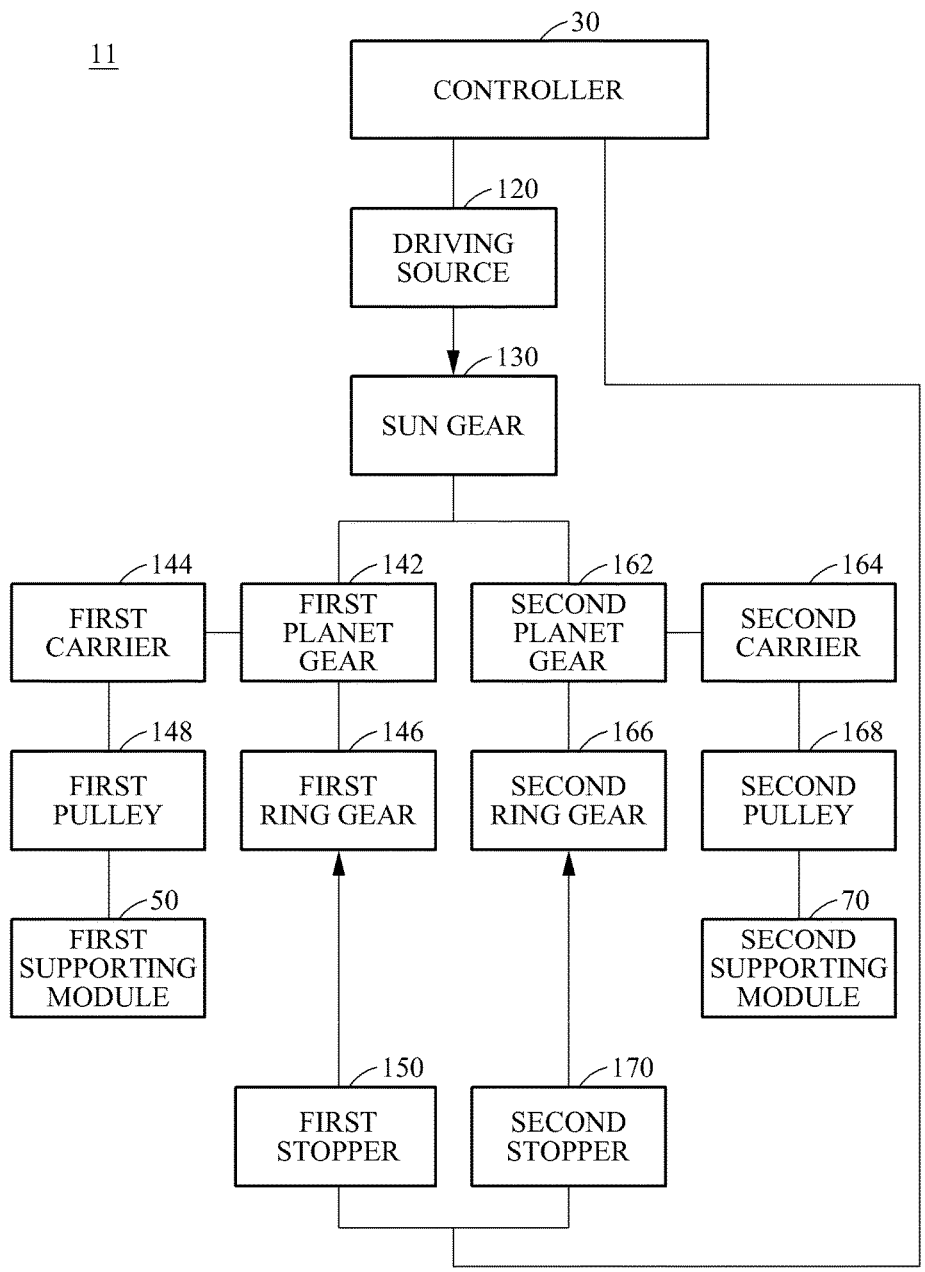

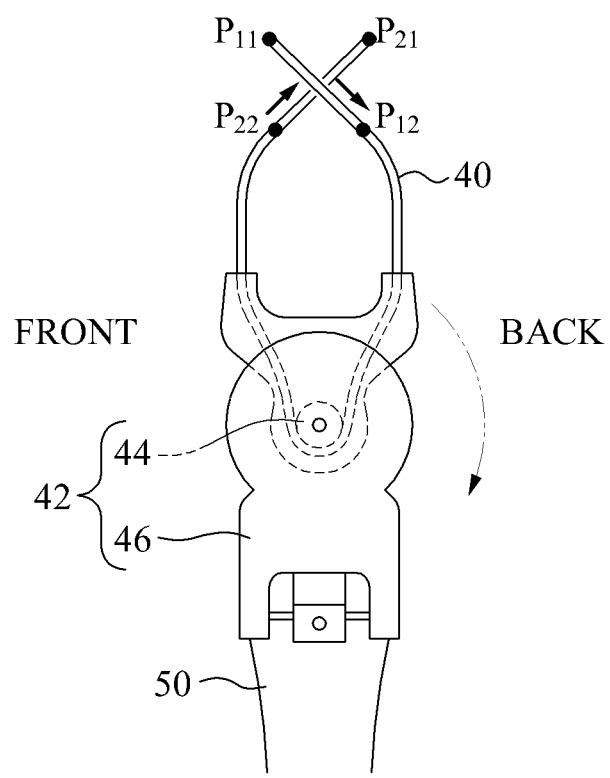

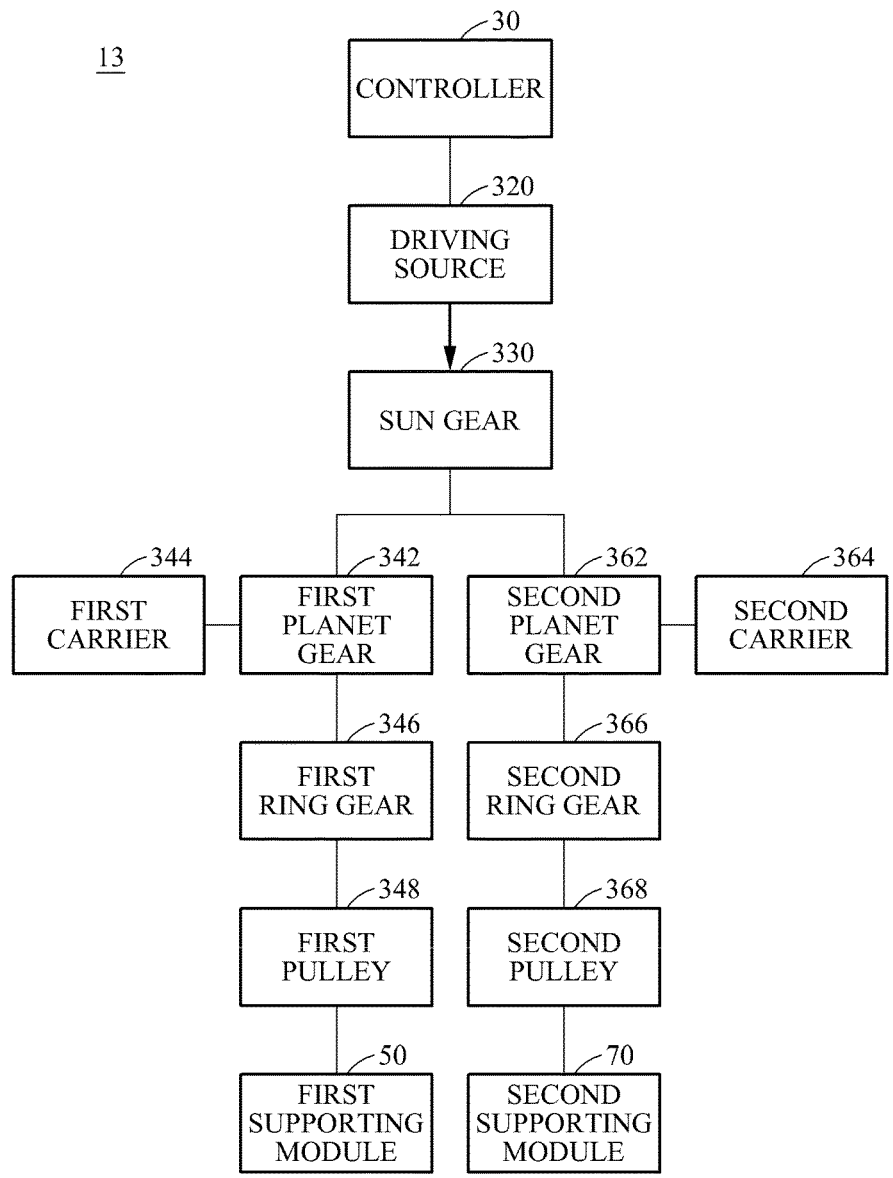

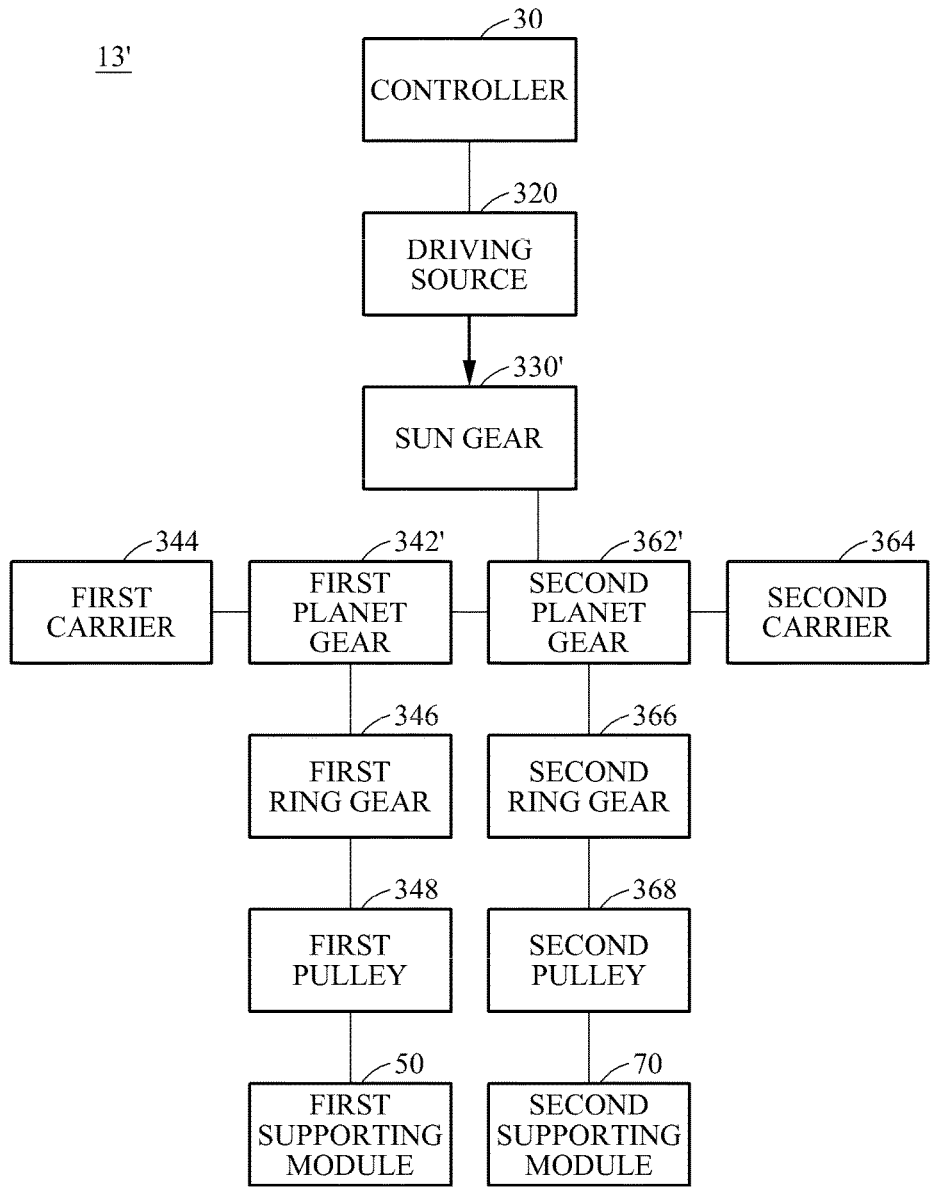

DRIVING MODULE, MOTION ASSISTANCE APPARATUS INCLUDING THE DRIVING MODULE, AND METHOD OF CONTROLLING THE MOTION ASSISTANCE APPARATUS

CROSS-REFERENCE TO RELATED APPLICATION

This application claims priority under 35 U.S.C. § 119 to Korean Patent Application No. 10-2014-0101743, filed on Aug. 7, 2014, in the Korean Intellectual Property Office, the disclosure of which is incorporated herein by reference in its entirety.

BACKGROUND

1. Field

Example embodiments relate to driving modules, motion assistance apparatuses including the driving modules, and/or methods of controlling the motion assistance apparatuses.

2. Description of the Related Art

With the onset of rapidly aging societies, many people are experiencing inconvenience and/or pain from joint problems, and interest in motion assistance apparatuses, which enable the elderly or patients with joint problems to walk with less effort, is growing. Furthermore, motion assistance apparatuses for intensifying muscular strength of human bodies may be useful for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and/or pedial frames disposed on feet of the users. The pelvic frames and femoral frames may be connected rotatably by hip joint portions, the femoral frames and sural frames may be connected rotatably by knee joint portions, and/or the sural frames and pedial frames may be connected rotatably by ankle joint portions.

The motion assistance apparatuses may include active joint structures including hydraulic systems and/or driving motors to drive each joint portion to improve muscular strength of legs of the users. For example, two individual motors to transmit driving power may be provided at left and right hip joint portions, respectively.

SUMMARY

At least one example embodiment relates to a driving module.

According to an example embodiment, a driving module includes a driving source configured to transmit power, an input side rotary body connected to the driving source and configured to rotate, and a first decelerator and a second decelerator configured to operate using the power received from the driving source through the input side rotary body. A gear ratio from the input side rotary body to an output terminal of the first decelerator may differ from a gear ratio from the input side rotary body to an output terminal of the second decelerator.

According to some example embodiments, at least one of the first decelerator and the second decelerator may include a planet gear connected to an outer circumferential surface of the input side rotary body and configured to at least one of rotate with respect to an axis of rotation thereof and revolve around the input side rotary body using the power received through the input side rotary body, a carrier connected to the axis of rotation of the planet gear and configured to rotate when the planet gear revolves around the input side rotary body, a ring gear including an inner circumferential surface, the inner circumferential surface configured to be connected to the planet gear, and a pulley configured to act as the output terminal of the at least one of the first decelerator and the second decelerator, the pulley including an outer circumferential surface over which a power transmitting member configured to transmit the power from the input side rotary body to another member connected to the driving module is to be wound.

According to some example embodiments, the first decelerator and the second decelerator may respectively include the planet gear, the carrier, the ring gear, and the pulley, and the planet gear of the first decelerator and the planet gear of the second decelerator may be fixed to perform a single rigid body motion.

According to some example embodiments, the pulley and the ring gear may be fixed to perform a single rigid body motion.

According to some example embodiments, the pulley and the ring gear are provided as an integral body such that the pulley is defined along on an outer circumferential surface of the ring gear.

According to some example embodiments, the carrier may be restricted exclusively by the axis of rotation of the planet gear, and the ring gear may be restricted exclusively by the planet gear and the pulley.

According to some example embodiments, the first decelerator and the second decelerator may respectively include the planet gear, the carrier, the ring gear, and the pulley, and the ring gear of the first decelerator and the ring gear of the second decelerator may be fixed together to perform a single rigid body motion.

According to some example embodiments, the pulley and the carrier may be fixed together to perform a single rigid body motion.

According to some example embodiments, the first decelerator may include a first planet gear, a first carrier, a first ring gear, and a first pulley, and the second decelerator may include a second planet gear, a second carrier, a second ring gear, and a second pulley.

According to some example embodiments, first two gears from among the first and second planet gears and the first and second ring gears may be fixed together to perform a single rigid body motion, and each of second two gears from among the first and second planet gears and the first and second ring gears may be fixed together to perform a single rigid body motion with each of the first and second pulleys, respectively.

At least one example embodiment relates to a motion assistance apparatus.

According to an example embodiment, a motion assistance apparatus includes a fixing member configured to be fixed to a user, a driving module on one side of the fixing member, the driving module including a driving source configured to transmit power, a first decelerator configured to operate based on the power received from the driving source, and a second decelerator configured to operate based on the power received from the driving source, a first joint member and a second joint member configured to assist respective rotary motions, a first power transmitting member connected to an output terminal of the first decelerator to the first joint member such that the output terminal of the first decelerator and the first joint member are enabled to have opposite rotation directions, and a second power transmitting member connected to an output terminal of the second decelerator to the second joint member such that the output terminal of the second decelerator and the second joint member are enabled to have identical rotation directions.

According to some example embodiments, the first power transmitting member and the second power transmitting member may be asymmetrically provided to each other with respect to the driving module.

According to some example embodiments, when seeing from respective sides of the motion assistance apparatus, the first power transmitting member may be provided in an overlapping manner between the driving module and the first joint member, and the second power transmitting member may be provided in a non-overlapping manner between the driving module and the second joint member.

According to some example embodiments, the first decelerator may include a first planet gear, a first carrier, a first ring gear, and a first pulley corresponding to the output terminal of the first decelerator, and the second decelerator may include a second planet gear, a second carrier, a second ring gear, and a second pulley corresponding to the output terminal of the second decelerator.

According to some example embodiments, first two gears from among the first and second planet gears and the first and second ring gears may be configured to perform single rigid body motion, and each of second two gears from among the first and second planet gears and the first and second ring gears may be configured to perform a single rigid body motion with each of the first and second pulleys, respectively.

At least one example embodiment relates to a motion assistance apparatus.

According to an example embodiment, a motion assistance apparatus includes a fixing member configured to be fixed to a user, a driving module on one side of the fixing member, the driving module including a driving source configured to transmit driving power, a first decelerator configured to operate using the power received from the driving source, and a second decelerator configured to operate using the power received from the driving source, a first joint member and a second joint member configured to assist respective rotary motions, a first power transmitting member connected to the first decelerator and the first joint member, and a second power transmitting member connected to the second decelerator to the second joint member. A gear ratio from the driving source to an output terminal of the first decelerator may differ from a gear ratio from the driving source to an output terminal of the second decelerator.

According to some example embodiments, the first power transmitting member may be provided between the output terminal of the first decelerator and the first joint member to enable the output terminal of the first decelerator and the first joint member to have opposite rotation directions, and the second power transmitting member may be provided between the output terminal of the second decelerator and the second joint member to enable the output terminal of the second decelerator and the second joint member to have identical rotation directions.

According to some example embodiments, the first decelerator may include a first planet gear, a first carrier, a first ring gear, and a first pulley corresponding to the output terminal of the first decelerator, the second decelerator including a second planet gear, a second carrier, a second ring gear, and a second pulley corresponding to the output terminal of the second decelerator, first two gears from among the first and second planet gears, the first and second ring gears being coupled together to perform a single rigid body motion, and each of second two gears from among the first and second planet gears, the first and second ring gears being fixed together to perform a single rigid body motion with each of the first and second pulleys, respectively.

According to some example embodiments, the motion assistance apparatus may further include a first supporting module connected to the first joint member to support the first portion of the user, and a second supporting module connected to the second joint member to support the second portion of the user.

According to some example embodiments, when the driving source is powered on, the first supporting module and the second supporting module may rotate at different angular velocities such that the first supporting module and the second supporting module are either spaced apart from each other or close to each other.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects of example embodiments will become apparent and more readily appreciated from the following description of some example embodiments, taken in conjunction with the accompanying drawings of which:

FIG. 6 is a block diagram illustrating a motion assistance apparatus according to an example embodiment;

FIG. 7B illustrates a forward movement of the first supporting module 50, viewed from a right side of FIG. 1, according to an example embodiment;

FIG. 18 is a block diagram illustrating a motion assistance apparatus according to an example embodiment;

FIG. 19 is a block diagram illustrating a motion assistance apparatus according to an example embodiment;

DETAILED DESCRIPTION

Figure 1:
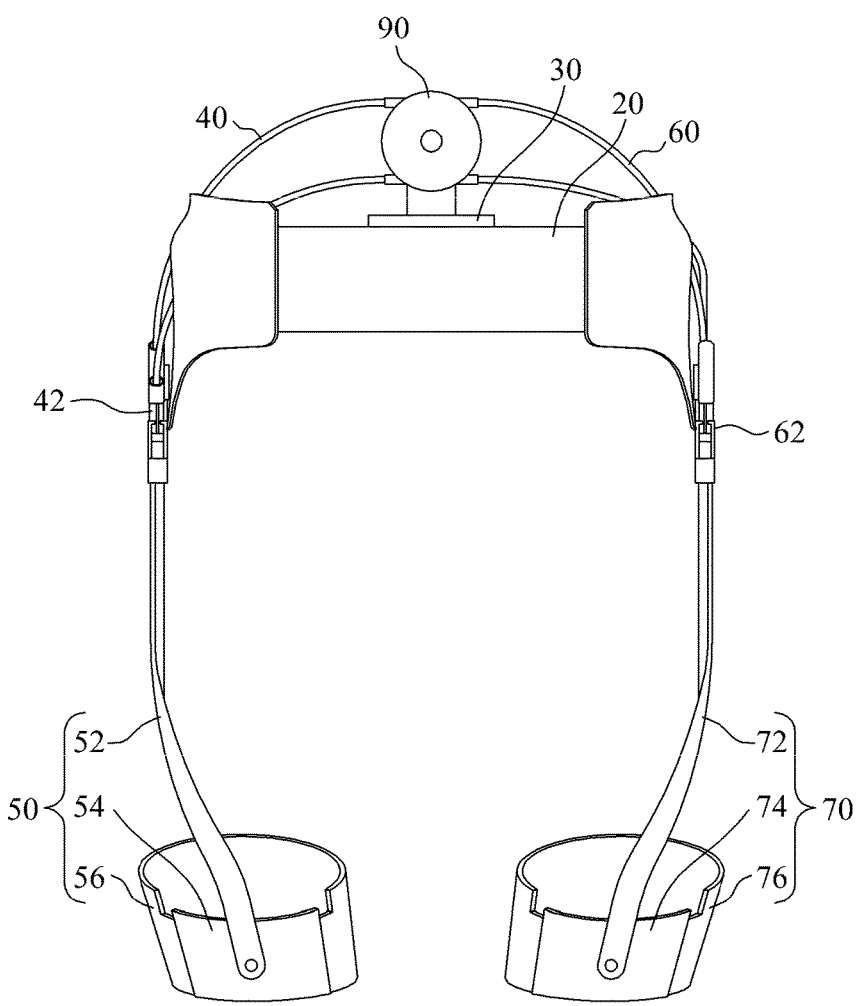
FIG. 1 is a front view illustrating a motion assistance apparatus according to an example embodiment.

Various example embodiments will now be described more fully with reference to the accompanying drawings. Example embodiments, however, may be embodied in many different forms and should not be construed as being limited to the example embodiments set forth herein. Rather, these example embodiments are provided so that this disclosure will be thorough and complete, and will fully convey the scope of example embodiments to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

A motion assistance apparatus according to example embodiments to be described hereinafter may simultaneously drive a plurality of supporting modules using a single driving source. The motion assistance apparatus may enable the plurality of supporting modules to have different relative positions using the single driving source.

According to an example embodiment, using a device configured to selectively apply or block power to be transmitted between the single driving source and the plurality of supporting modules, the plurality of supporting modules may have different relative positions.

According to an example embodiment, by setting different gear ratios of power to be transmitted between the single driving source and the plurality of supporting modules, the plurality of supporting modules may have different relative positions.

Figure 2:
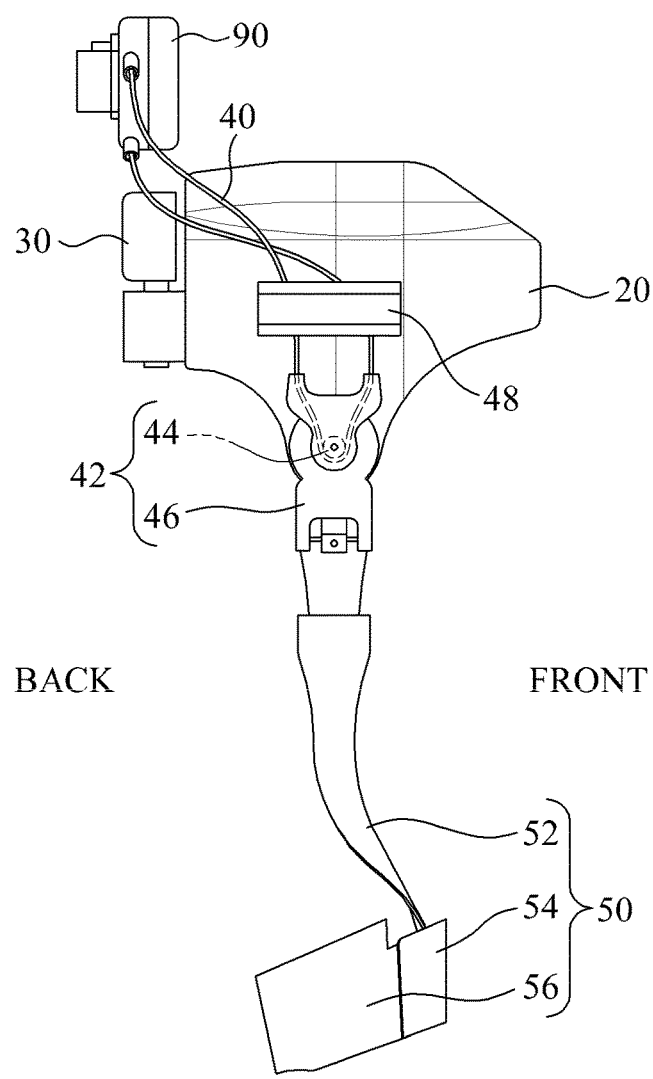
FIG. 2 is a left side view illustrating a motion assistance apparatus according to an example embodiment.
Figure 3:
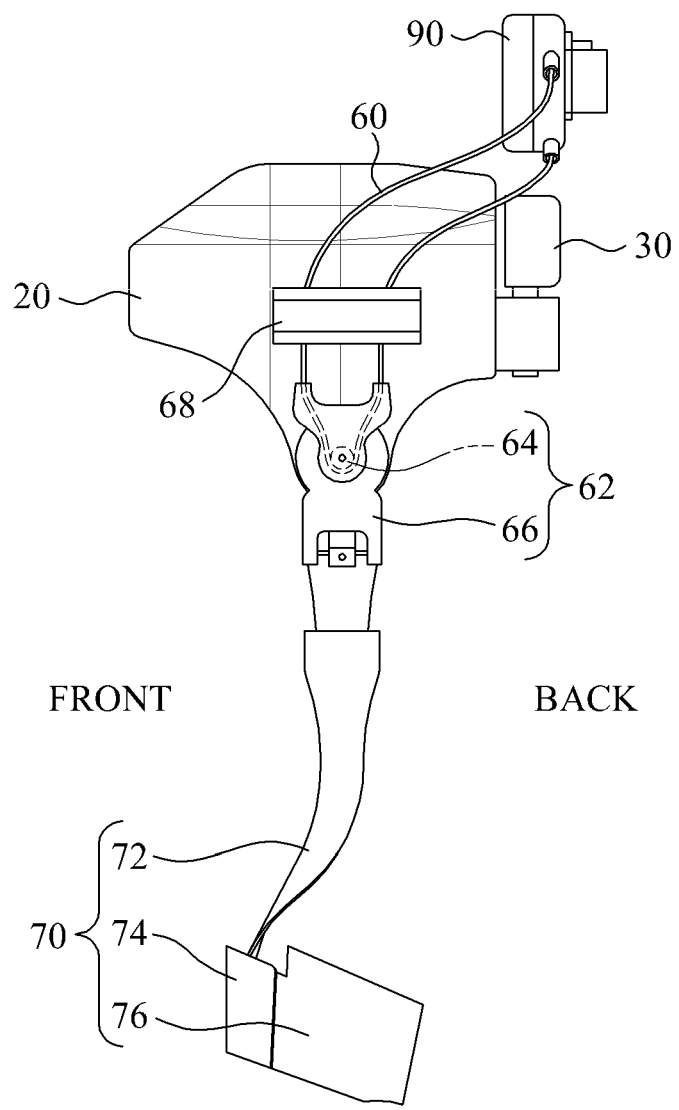
FIG. 3 is a right side view illustrating a motion assistance apparatus according to an example embodiment.

FIGS. 1 through 3 illustrate a motion assistance apparatus common to various example embodiments. FIGS. 4 through 14B illustrate some example embodiments including a device configured to selectively apply or block power to be transmitted between a single driving source and a plurality of supporting modules. FIGS. 15 through 27B illustrate some example embodiments in which different gear ratios are set with respect to power to be transmitted between a single driving source and a plurality of supporting modules. Hereinafter, example embodiments will be described with reference to the drawings.

FIG. 1 is a front view illustrating a motion assistance apparatus according to an example embodiment, FIG. 2 is a left side view illustrating the motion assistance apparatus according to an example embodiment, and FIG. 3 is a right side view illustrating the motion assistance apparatus according to an example embodiment.

Referring to FIGS. 1 through 3, a motion assistance apparatus 10 may be worn by a user to assist a motion of the user.

The user may correspond to a human, an animal, or a robot. However, the user is not limited thereto. Further, although FIG. 1 illustrates a case in which the motion assistance apparatus 10 assists a motion of a thigh of the user, the motion assistance apparatus 10 may also assist a motion of another part of an upper body (e.g., a hand, an upper arm, or a lower arm) of the user, or a motion of another part of a lower body (e.g., a foot, or a calf) of the user. The motion assistance apparatus 10 may assist a motion of a part of the user.

Hereinafter, a case in which the motion assistance apparatus 10 assists a motion of a thigh of a human will be described.

The motion assistance apparatus 10 includes a fixing member 20, a driving module 90, a controller 30, a first power transmitting member 40, a second power transmitting member 60, and a plurality of supporting modules including a first supporting module 50 and a second supporting module 70.

The fixing member 20 may be fixed to the user. The fixing member 20 may be in contact with at least a portion of an outer surface of the user. The fixing member 20 may be provided to cover the outer surface of the user. The fixing member 20 may be curved to conform to a contact portion of the user. The fixing member 20 may include a curved surface to be in contact with the user. For example, the fixing member 20 may be fixed to one side of a waist of the user.

The driving module 90 may transmit power of a single driving source to the first supporting module 50 and the second supporting module 70. The driving module 90 may be provided on one side of the fixing member 20. For example, referring to FIG. 1, the driving module 90 may be provided on a rear side of the fixing member 20. The driving module 90 may be provided on an upper side of the fixing member 20. The driving module 90 may be disposed to be spaced apart from the first supporting module 50 and the second supporting module 70. The driving module 90 may be disposed on an opposite side of the first supporting module 50 and the second supporting module 70 with respect to the fixing member 20. According to the foregoing structure, a volume of a product to be disposed on a joint portion may be reduced. However, a position of the driving module 90 is not limited thereto. The driving module 90 will be described in detail later.

The controller 30 may control the driving module 90 to transmit power to the first supporting module 50 and the second supporting module 70. The controller 30 may be provided on one side of the fixing member 20. For example, referring to FIG. 1, the controller 30 may be provided on the rear side of the fixing member 20. The controller 30 may be provided on the upper side of the fixing member 20. However, a position of the controller 30 is not limited thereto.

The first power transmitting member 40 may be disposed between the driving module 90 and the first supporting module 50, and the second power transmitting member 60 may be disposed between the driving module 90 and the second supporting module 70. The first power transmitting member 40 may transmit power from the driving module 90 to the first supporting module 50, and the second power transmitting member 60 may transmit power from the driving module 90 to the second supporting module 70. The first power transmitting member 40 and the second power transmitting member 60 may respectively transmit power using, for example, a pushing or pulling force, or transmit power using a frictional force, a tensile force, or an elastic force. For example, the first power transmitting member 40 and the second power transmitting member 60 may respectively include, for example, a wire, a cable, a string, a rubber band, a spring, a belt, and a chain.

For example, power input terminals of the first power transmitting member 40 and the second power transmitting member 60 may be connected to the driving module 90, and power output terminals of the first power transmitting member 40 and the second power transmitting member 60 may be connected to a first joint assembly 42 connected to the first supporting module 50 and a second joint assembly 62 connected to the second supporting module 70, respectively.

The first joint assembly 42 may transmit power between the first power transmitting member 40 and the first supporting module 50, and the second joint assembly 62 may transmit power between the second power transmitting member 60 and the second supporting module 70. The first joint assembly 42 may be connected to the first power transmitting member 40 and the first supporting module 50, and the second joint assembly 62 may be connected to the second power transmitting member 60 and the second supporting module 70.

The first joint assembly 42 includes a first joint member 44, and a first connecting member 46.

The first joint member 44 may be configured to rotate using power received from the first power transmitting member 40. The first joint member 44 may be disposed on one side of a hip joint of the user. The first joint member 44 may also be referred to as a "hip joint assistance member".

The first connecting member 46 may couple the first joint member 44 to the first supporting module 50. One side of the first connecting member 46 may be coupled to the first joint member 44, and another side of the first connecting member 46 may be coupled to the first supporting module 50.

The first connecting member 46 may be configured to rotate using torque of the first joint member 44. The first connecting member 46 may be fastened with the first joint member 44 by a separate fastening member, or the first connecting member 46 and the first joint member 44 may be provided as an integral body.

The other side of the first connecting member 46 may be hinge-connected to the first supporting module 50. The other side of the first connecting member 46 and the first supporting module 50 may be connected to each other using a hinge connection structure. A hinge axis of the hinge connection structure may intersect an axis of rotation of the first joint member 44. For example, the hinge axis of the hinge connection structure and the axis of rotation of the first joint member 44 may be orthogonal to each other. Thus, the first supporting module 50 may perform a two degree of freedom motion with respect to the fixing member 20 by the hinge axis and the axis of rotation.

Similar to the first joint assembly 42, the second joint assembly 62 includes a second joint member 64, and a second connecting member 66. Detailed descriptions of the second joint member 64 and the second connecting member 66 will be omitted for conciseness.

The first power transmitting member 40 may transmit power from the driving module 90 to the first supporting module 50, and the second power transmitting member 60 may transmit power from the driving module 90 to the second supporting module 70.

The first power transmitting member 40 and the second power transmitting member 60 may be asymmetrically connected to each other with respect to the driving module 90.

For Example, the first power transmitting member 40 may be provided in an overlapping manner, when seeing when seeing from a side of the motion assistance apparatus 10, between the driving module 90 and the first supporting module 50. By contrast, the second power transmitting member 60 may be provided in a non-overlapping manner, when seeing from a side of the motion assistance apparatus 10, between the driving module 90 and the second supporting module 70. As shown in FIG. 2, the first power transmitting member 40 may be provided in a "shape of X", and as shown in FIG. 3, the second power transmitting member 40 may be provided in parallel to each other, for example, in a "shape of II".

Referring to FIG. 2, a first portion of the first power transmitting member 40 may be connected to an upper side of the driving module 90 and a rear portion of the first supporting module 50. A second portion of the first power transmitting member 40 may be connected to a lower side of the driving module 90 and a front portion of the first supporting module 50. In this example, the first portion and the second portion of the first power transmitting member 40 may be provided to cross each other when seeing from a side of the motion assistance apparatus 10.

Referring to FIG. 3, a first portion of the second power transmitting member 60 may be connected to the upper side of the driving module 90 and a front portion of the second supporting module 70. A second portion of the second power transmitting member 60 may be connected to the lower side of the driving module 90 and a rear portion of the second supporting module 70. In this example, the first portion and the second portion of the second power transmitting member 60 may be provided to not cross each other when seeing from a side of the motion assistance apparatus 10. The first portion and the second portion of the second power transmitting member 60 may be provided to be parallel to each other.

Accordingly, the first power transmitting member 40 may enable two rotary bodies connected thereto to have opposite rotation directions, and the second power transmitting member 60 may enable two rotary bodies connected thereto to have identical rotation directions.

The disposition of the first power transmitting member 40 and the second power transmitting member 60 is not limited thereto. Both of the first power transmitting member 40 and the second power transmitting member 60 may be provided such that the first and second portions of the respective power transmitting members are provided to cross each other, or are provided to not cross each other.

A shield 48 may be provided on one side of the first power transmitting member 40 to cover at least a portion of the first power transmitting member 40, and a shield 68 may be provided on one side of the second power transmitting member 60 to cover at least a portion of the second power transmitting member 60. The shields 48 and 68 may be disposed on both sides of the fixing member 20, respectively. The first power transmitting member 40 may pass through the shield 48 to be connected to the first supporting module 50, and the second power transmitting member 60 may pass through the shield 68 to be coupled to the second supporting module 70. The shield 48 may prevent or mitigate an external exposure of a portion of the first power transmitting member 40, and the shield 68 may prevent an external exposure of a portion of the second power transmitting member 60. Through the shields 48 and 68, the first power transmitting member 40 and the second power transmitting member 60 may operate without being obstructed by clothing while the user is wearing the clothing over the shields 48 and 68. The shields 48 and 68 may respectively include a hanging recess for hanging a waist band of the clothing.

Tubes may be provided in external portions of the first power transmitting member 40 and the second power transmitting member 60, respectively. The tubes may guide the first power transmitting member 40 and the second power transmitting member 60. The tubes may be disposed between the driving module 90 and the first supporting module 50, and between the driving module 90 and the second supporting module 70, respectively. Through the tubes, the first power transmitting member 40 and the second power transmitting member 60 may operate without being obstructed by clothing while the user is wearing the clothing over the tubes. The tubes may be formed of a flexible material (e.g., rubber and silicone), or a rigid material (e.g., plastic and steel). The tubes may prevent a direct contact between the first power transmitting member 40 and the user and a direct contact between the second power transmitting member 60 and the user, thereby increasing a wearability.

The first supporting module 50 and the second supporting module 70 may support portions of the user. The first supporting module 50 and the second supporting module 70 may assist motions of the portions of the user. The first supporting module 50 and the second supporting module 70 may rotate using power received from the first power transmitting member 40 and the second power transmitting member 60, respectively. Torque of the first supporting module 50 and torque of the second supporting module 70 may be transmitted to the portions of the user to assist the motions of the portions of the user.

The first supporting module 50 may support a portion of the user, and the second supporting module 70 may support another portion of the user.

For example, the first supporting module 50 may support a right leg of the user, and the second supporting module 70 may support a left leg of the user.

The first supporting module 50 includes a first supporting frame 52, a first pressurizing member 54, and a first supporting member 56.

The first supporting frame 52 may be rotatably connected to the first joint member 42.

The first pressurizing member 54 may be connected to one side of the first supporting frame 52. For example, the first pressurizing member 54 may be disposed on one side of the right leg of the user to push or pull a right thigh of the user. The first pressurizing member 54 may be disposed on a front surface of the right thigh of the user.

The first supporting member 56 may be connected to one side of the first pressurizing member 54. For example, the first supporting member 56 may be disposed to cover a circumference of at least a portion of the right thigh of the user to prevent a separation between the right thigh of the user and the first supporting frame 52. The first supporting member 56 may be disposed on an opposite side of the first pressurizing member 54 with respect to the right thigh of the user.

Similar to the first supporting module 50, the second supporting module 70 includes a second supporting frame 72, a second pressurizing member 74, and a second supporting member 76. Detailed descriptions of the second supporting frame 72, the second pressurizing member 74, and the second supporting member 76 will be omitted for conciseness.

The first joint assembly 42, the second joint assembly 62, the first supporting frame 52, and the second supporting frame 72 may be omitted. Accordingly, the first power transmitting member 40 may connect the driving module 90 directly to the first supporting member 56, and the second transmitting member 40 may connect the driving module 90 directly to the second supporting member 76. The first power transmitting member 40 may move the first supporting member 56 by directly pushing or pulling the first supporting member 56, and the second power transmitting member 60 may move the second supporting member 76 by directly pushing or pulling the second supporting member 76.

Figure 4:
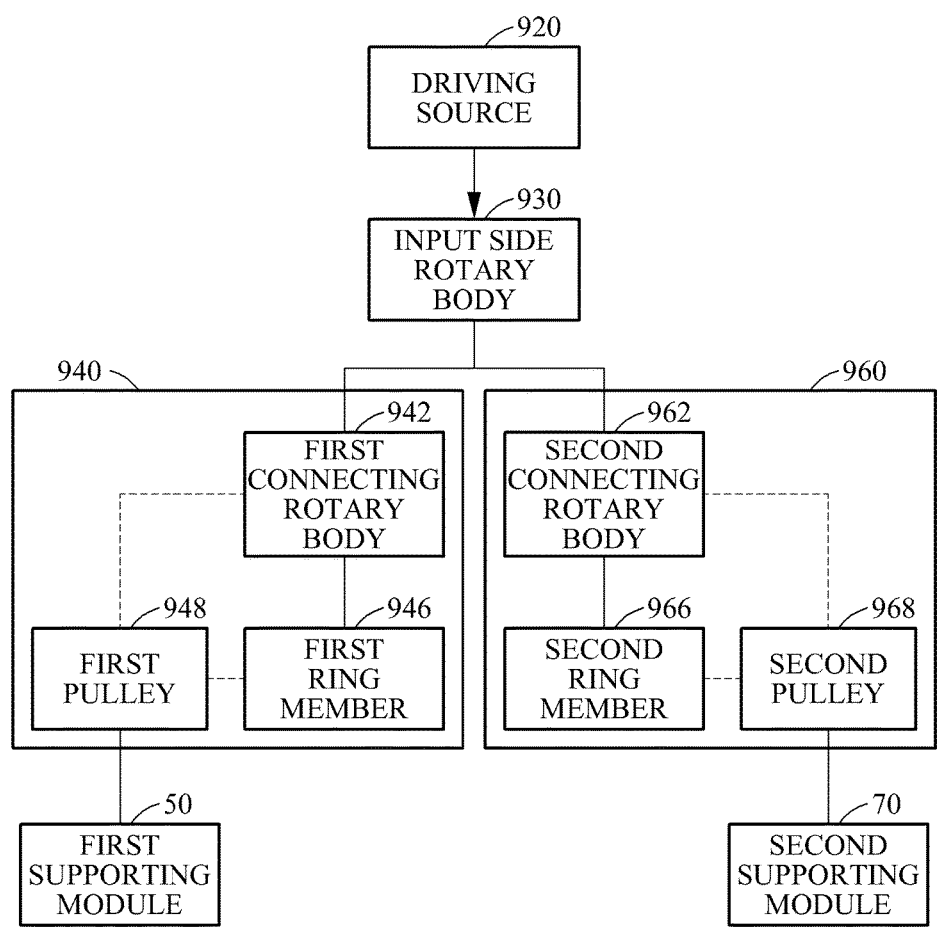
FIG. 4 is a block diagram illustrating a driving module according to an example embodiment.

FIG. 4 is a block diagram illustrating a driving module according to an example embodiment.

Referring to FIG. 4, the driving module 90 includes a driving source 920, an input side rotary body 930, and two decelerators, which include a first decelerator 940 and a second decelerator 960, configured to receive power from the input side rotary body 930 and transmit the power to the first supporting module 50 and the second supporting module 70, respectively.

For example, the first decelerator 940 and the second decelerator 960 may use a three (3)-port system, which includes a single input terminal and two output terminals. The first decelerator 940 includes a first connecting rotary body 942, a first ring member 946, and a first pulley 948, and the second decelerator 960 includes a second connecting rotary body 962, a second ring member 966, and a second pulley 968. The first pulley 948 may be connected to the first connecting rotary body 942 or the first ring member 946 to transmit power to the first supporting module 50, and the second pulley 968 may be connected to the second connecting rotary body 962 or the second ring member 966 to transmit power to the second supporting module 70.

The first decelerator 940 and the second decelerator 960 configured by the 3-port system are described. However, types of the first decelerator 940 and the second decelerator 960 are not limited thereto. For example, when the first decelerator 940 and the second decelerator 960 transmit power in a structure of toothed gears, the input side rotary body 930, the first and second connecting rotary bodies 942 and 962, and the first and second ring members 946 and 966 may correspond to a "linear gear", "planet gears", and "ring gears", respectively. For example, when the first decelerator 940 and the second decelerator 960 transmit power by rolling friction, the input side rotary body 930, the first and second connecting rotary bodies 942 and 962, and the first and second ring members 946 and 966 may correspond to a "primary pulley", "secondary pulleys", "tertiary pulleys". In an example, when the first decelerator 940 and the second decelerator 960 transmit power by a harmonic drive structure, the input side rotary body 930, the first and second connecting rotary bodies 942 and 962, and the first and second ring members 946 and 966 may correspond to a "wave generator," "flexsplines," and "circular splines," respectively.

Hereinafter, a case in which the first decelerator 940 and the second decelerator 960 transmit power in a structure of toothed gears will be described. However, it is obvious that example embodiments are not limited to the following description.

Figure 5:
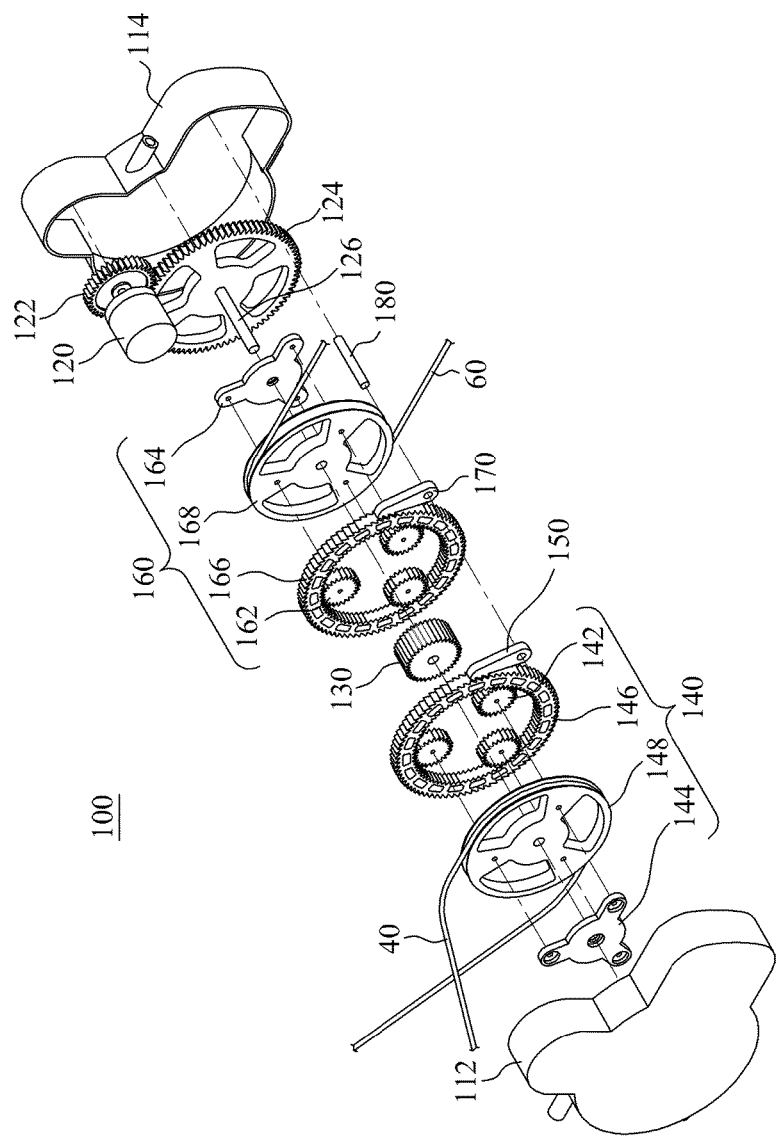
FIG. 5 is a front exploded perspective view illustrating a driving module according to an example embodiment.

FIG. 5 is a front exploded perspective view illustrating a driving module according to an example embodiment.

Referring to FIG. 5, a driving module 100 includes a first case 112, a second case 114, a driving source 120, a sun gear 130, a first decelerator 140, a first stopper 150, a second decelerator 160, a second stopper 170, and a stopper shaft 180.

The first case 112 and the second case 114 may form an appearance of the driving module 100. The first case 112 and the second case 114 may prevent a direct contact between inner components of the driving module 100 and a user, thereby increasing a wearability.

The driving source 120 may include, for example, a motor configured to receive a voltage or a current and generate power, or a pump operated by a fluid pressure. However, types of the driving source 120 are not limited thereto.

The driving source 120 includes a driving gear 122 configured to receive power from the driving source 120, a decelerating gear 124 connected to the driving gear 122 to decelerate a rotation velocity, and a sun gear shaft 126 configured to transmit power to the sun gear 130.

The sun gear 130 may be coupled to the sun gear shaft 126 to transmit power to the first decelerator 140 and the second decelerator 160 simultaneously. An axis of rotation of the sun gear 130 may match an axis of rotation of the first decelerator 140 and an axis of rotation of the second decelerator 160.

Although FIG. 5 illustrates a single sun gear 130, a plurality of sun gears 130 may be provided, and each of the plurality of sun gears 130 may transmit power to the first decelerator 140 and the second decelerator 160. For example, the plurality of sun gears 130 may be configured to perform a single rigid body motion.

The first decelerator 140 includes a first planet gear 142, a first carrier 144, a first ring gear 146, and a first pulley 148.

The first planet gear 142 may be coupled to the sun gear 130 and the first ring gear 146. The first planet gear 142 may be engaged with the sun gear 130 and the first ring gear 146. The first planet gear 142 may be engaged to an outer circumferential surface of the sun gear 130. Further, the first planet gear 142 may be engaged to an inner circumferential surface of the first ring gear 146. Thus, the first planet gear 142 may interact with, for example, the sun gear 130 or the first ring gear 146. The first planet gear 142 may rotate using torque received from, for example, the sun gear 130 or the first ring gear 146.

At least one first planet gear 142 may be disposed. When a plurality of first planet gears 142 is provided, the first planet gears 142 may be disposed at identical angles with respect to the axis of rotation of the sun gear 130.

The first carrier 144 may be coupled to an axis of rotation of the first planet gear 142. The first carrier 144 may be coupled to axes of rotation of the plurality of first planet gears 142. The first carrier 144 may be coupled to both the axis of rotation of the first planet gear 142 and the axis of rotation of the sun gear 130.

In the foregoing structure, the first carrier 144 may rotate when the first planet gear 142 revolves around the sun gear 130. Conversely, the first carrier may not rotate when the first planet gear 142 does not revolve around the sun gear 130.

The first ring gear 146 may be coupled to the first planet gear 142. The first ring gear 146 may be engaged with the first planet gear 142. The first ring gear 146 may rotate using torque received from the first planet gear 142. The first ring gear 146 includes an inner surface to be coupled to the first planet gear 142, and an outer surface to be coupled to the first stopper 150. For example, the inner surface and/or the outer surface of the first ring gear 146 may include teeth.

The first pulley 148 may transmit power to the first power transmitting member 40. The first power transmitting member 40 may be wound on an outer surface of the first pulley 148.

The first pulley 148 may rotate using torque received from the first carrier 144. A rotation velocity and a rotation direction of the first pulley 148 may be identical to a rotation velocity and a rotation direction of the first carrier 144. The first pulley 148 and the first carrier 144 may perform a single rigid body motion. For example, the first pulley 148 may be fastened with the first carrier 144 by a separate fastening member, or the first pulley 148 and the first carrier 144 may form an integral body.

The first stopper 150 may enable the first ring gear 146 to selectively rotate. The first stopper 150 may selectively restrict the rotation of the first ring gear 146. For example, the first stopper 150 may include teeth corresponding to the teeth provided on the outer surface of the first ring gear 146.

A state in which the first stopper 150 is engaged to the first ring gear 146 may be referred to as a "restriction state", and a state in which the first stopper 150 is separated from the first ring gear 146 may be referred to as a "release state".

The first stopper 150 may rotate on the stopper shaft 180. Based on a rotation angle of the first stopper 150, the first stopper 150 may selectively enable the rotation of the first ring gear 146.

Similar to the first decelerator 140, the second decelerator 160 includes a second planet gear 162, a second carrier 164, a second ring gear 166, and a second pulley 168. Detailed descriptions of the second planet gear 162, the second carrier 164, the second ring gear 166, and the second pulley 168 will be omitted for conciseness. For example, the first decelerator 140 and the second decelerator 160 may be disposed in mirror images.

Similar to the first stopper 150, the second stopper 170 may enable the second ring gear 166 to selectively rotate. A detailed description of the second stopper 170 will be omitted for conciseness.

The stopper shaft 180 may function as a central axis of rotation of the first stopper 150 and/or the second stopper 170. The stopper shaft 180 may be fixed to the first case 112 and/or the second case 114.

Although the driving gear 122, the decelerating gear 124, the sun gear 130, the first planet gear 142, the second planet gear 162, the first ring gear 146, and the second ring gear 166 are illustrated as toothed gears, example embodiments are not limited thereto. The driving gear 122, the decelerating gear 124, the sun gear 130, the first planet gear 142, the second planet gear 162, the first ring gear 146, and the second ring gear 166 may be rotary bodies capable of transmitting power by rolling friction.

FIG. 6 is a block diagram illustrating a motion assistance apparatus according to an example embodiment.

Referring to FIG. 6, a motion assistance apparatus 11 may operate as follows.

A controller 30 may control (e.g., power on) the driving source 120 to transmit power to the sun gear 130. The controller 30 may operate the first stopper 150 and the second stopper 170 to be selectively connected to the first ring gear 146 and the second ring gear 166, respectively.

According to the operation of the first stopper 150, the first supporting module 50 may selectively rotate.

To operate the first supporting module 50, a force greater than a load applied to the first supporting module 50 is desired to be applied to the first supporting module 50. The load may be transmitted through the first power transmitting member 40 and the first pulley 148 to the first carrier 144. Accordingly, a load greater than or equal to a threshold level may exist in the first carrier 144. Hereinafter, descriptions will be provided based on the foregoing premise.

When the first stopper 150 is engaged to the first ring gear 146, a rotation of the first ring gear 146 may be stopped. When power received from the sun gear 130 increases sufficiently, the first planet gear 142 may overcome a load applied to the first carrier 144, and revolve around the sun gear 130. In response to the revolution of the first planet gear 142, the first carrier 144 and the first pulley 148 may rotate. When the first pulley 148 rotates, the power may be transmitted through the first power transmitting member 40, and the first supporting module 50 may rotate.

When the first stopper 150 is separated from the first ring gear 146, the first ring gear 146 may be prepared to rotate. The first ring gear 146 may be in an idling condition. The power received from the sun gear 130 may be transmitted through the first planet gear 142 to the first ring gear 146 being in the idling condition, and the first ring gear 146 may rotate. In this example, the first carrier 144, the first pulley 148, the first power transmitting member 40, and the first supporting module 50 may not rotate.

Accordingly, the first supporting module 50 may selectively rotate based on the operation of the first stopper 150.

Similarly, the second supporting module 70 may selectively rotate based on the operation of the second stopper 170. Detailed descriptions will be omitted for conciseness.

By alternately engaging the first stopper 150 and the second stopper 170 to the first ring gear 146 and the second ring gear 166, respectively, the first supporting module 50 and the second supporting module 70 may alternately rotate. By alternately engaging the first stopper 150 and the second stopper 170 to the first ring gear 146 and the second ring gear 166, respectively, a walking motion of a user may be assisted.

Figure 7A:
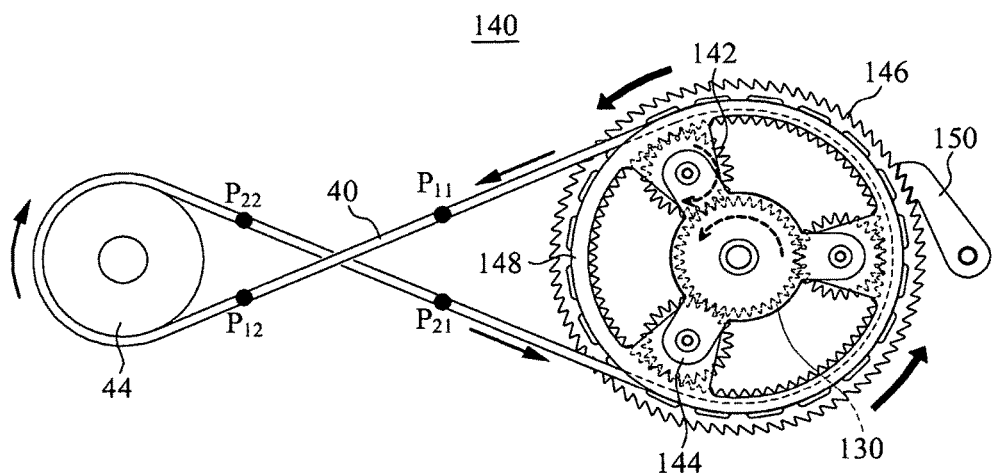
FIG. 7A illustrates an operation of a first decelerator associated with a forward movement of a first supporting module viewed from a front FIG. 1.

FIG. 7A illustrates an operation of the first decelerator 140 associated with a forward movement of the first supporting module, viewed from a front of FIG. 1, when the first supporting module 50 makes a forward movement, and FIG. 7B illustrates a forward movement operation of the first supporting module 50, viewed from a right side of FIG. 1, according to an example embodiment.

Figure 8A:
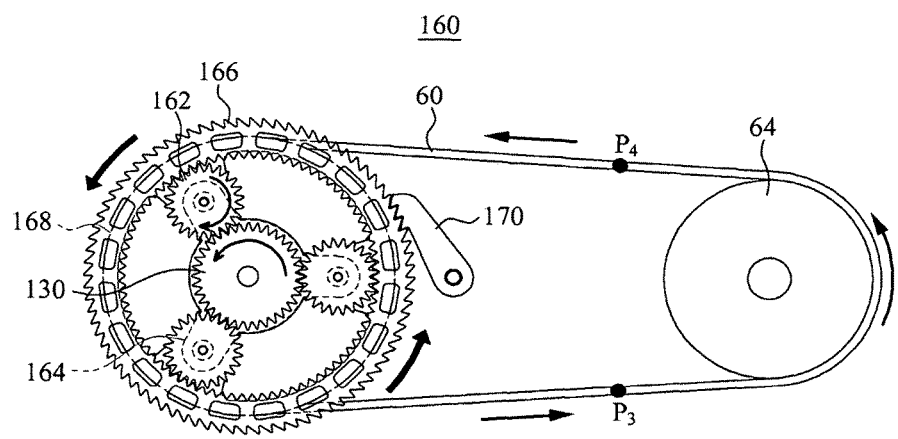
FIG. 8A illustrates an operation of a second decelerator, viewed from the front of FIG. 1, when a second supporting module makes a forward movement.
Figure 8B:
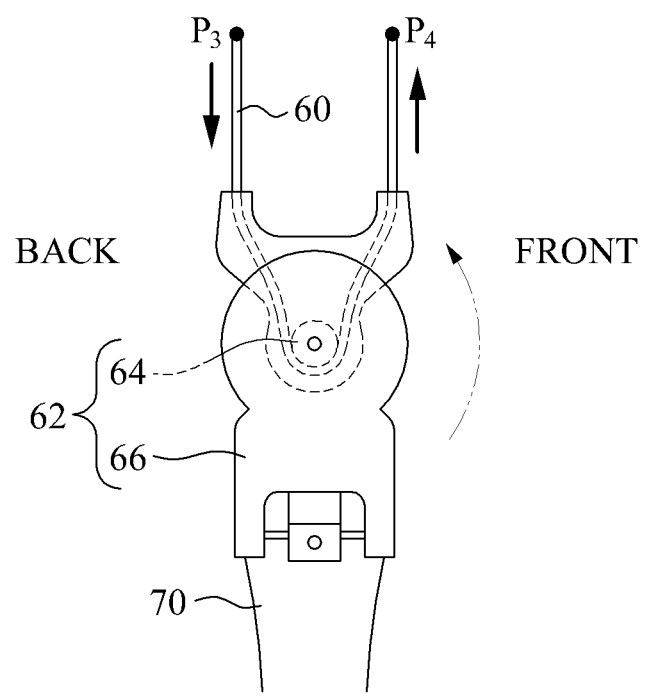
FIG. 8B illustrates an operation of the second supporting module, viewed from a left side of FIG. 1, when the second supporting module makes the forward movement according to an example embodiment.

FIG. 8A illustrates an operation of the second decelerator 160, viewed from the front of FIG. 1, when the second supporting module 70 makes a forward movement and FIG. 8B illustrates an operation of the second supporting module 70, viewed from a left side of FIG. 1, when the second supporting module 70, makes a forward movement.

Points $P_{11}$, $P_{12}$, $P_{21}$, $P_{22}$, $P_3$, and $P_4$ shown in FIGS. 7A through 8B are marked for ease of understanding of the drawings and thus, detailed descriptions of the points will be omitted for conciseness.

FIGS. 7A and 7B illustrate the first stopper 150 engaged to the first ring gear 146, and FIGS. 8A and 8B illustrate the second stopper 170 engaged to the second ring gear 166.

Accordingly, the first ring gear 146 and the second ring gear 166 may be selectively stopped.

Referring to FIGS. 7A through 8B, when the sun gear 130 rotates in one direction, the first supporting module 50 and the second supporting module 70 may move forward.

For example, when the sun gear 130 rotates counterclockwise with respect to the front of FIG. 1, the first planet gear 142 and the second planet gear 162 may rotate clockwise, the first carrier 144 and the second carrier 164 may rotate counterclockwise, and the first pulley 148 and the second pulley 168 may rotate counterclockwise.

Referring to FIGS. 7A and 7B, the first power transmitting member 40, which is provided in a twisted manner between the first pulley 148 and the first joint member 44, may enable the first joint member 44 to rotate in a direction opposite to the rotation direction of the first pulley 148. The first joint member 44 may be disposed on a right leg of a user. For example, the first joint member 44 may be disposed so that a surface of the first joint member 44 may face a right side surface of the right leg of the user. Thus, the first joint member 44 may enable the first supporting module 50 to move forward.

As shown in FIGS. 8A and 8B, the second power transmitting member 40, which is provided in a non-twisted manner between the second pulley 168 and the second joint member 64, may enable the second joint member 64 to rotate in a direction identical to the rotation direction of the second pulley 168. The second joint member 64 may be disposed on a left leg of the user. For example, the second joint member 64 may be disposed so that a surface of the second joint member 64, shown in FIG. 8A, may face a left side surface of the left leg of the user. In this example, the second joint member 64 may enable the second supporting module 70 to move forward.

When the sun gear 130 rotates in another direction (e.g., a direction opposite to the one direction), the first supporting module 50 and the second supporting module 70 may move backward. For example, when the sun gear 130 rotates clockwise with respect to the front of FIG. 1, the first supporting module 50 and the second supporting module 70 may move backward. Detailed descriptions will be omitted for conciseness.

Through the foregoing configuration, the first stopper 150 and the second stopper 170 may operate using various methods depending on states of the user.

First, both the first stopper 150 and the second stopper 170 may be in a restriction state. In this state, when the sun gear 130 rotates in one direction, the first supporting module 50 and the second supporting module 70 may move forward. When the sun gear 130 rotates in another direction (e.g., a direction opposite to the one direction), the first supporting module 50 and the second supporting module 70 may move backward.

By moving the first supporting module 50 and the second supporting module 70 forward, a sitting-down motion of the user may be assisted. Conversely, by moving the first supporting module 50 and the second supporting module 70 backward, a standing-up motion of the user may be assisted.

Second, the first stopper 150 and the second stopper 170 may operate alternately. For example, by engaging the first stopper 150 to the first ring gear 146 and separating the second stopper 170 from the second ring gear 166 while the sun gear 130 is rotating in one direction, the first supporting module 50 may move forward. Similarly, by separating the first stopper 150 from the first ring gear 146 and engaging the second stopper 170 to the second ring gear 166, the second supporting module 70 may move forward.

Through an asymmetric connection structure of the first power transmitting member 40 and the second power transmitting member 60, a walking motion may be assisted without changing a rotation direction of the sun gear 130.

Third, both the first stopper 150 and the second stopper 170 may be in a release state. While the driving source 120 is powered off, the first stopper 150 and the second stopper 170 may be maintained in the release state. In this state, the user may freely move without being affected by a load applied by the driving source 120.

The three motion states described above may be summarized as shown in Table 1.

TABLE 1

| | Motion state | First stopper | Second stopper |
|---|---|---|---|
| | Sitting-down/Standing-up | Restriction | Restriction |
| Walking | First supporting module movement | Restriction | Release |
| | Second supporting module movement | Release | Restriction |
| | Free motion | Release | Release |

Hereinafter, the same name may be used to describe an element, which has a same or similar function to the element included in the example embodiments described above. Unless otherwise mentioned, the descriptions on the foregoing example embodiments also may be applicable to the following example embodiments and thus, duplicated descriptions will be omitted for conciseness.

Figure 9:
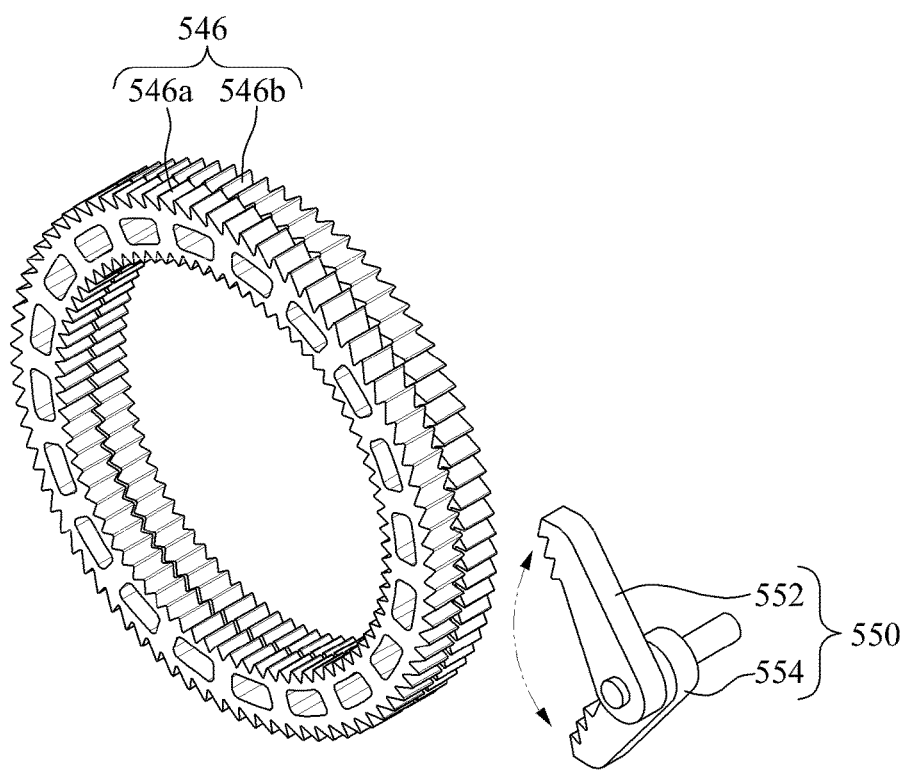
FIG. 9 is a view illustrating a ring gear and a stopper according to an example embodiment.

FIG. 9 is a view illustrating a ring gear and a stopper according to an example embodiment.

Referring to FIG. 9, a ring gear 546 includes a first compound ring gear 546a and a second compound ring gear 546b. The first compound ring gear 546a and the second compound ring gear 546b may have identical rotation directions and identical rotation velocities. The first compound ring gear 546a and the second compound ring gear 546b may be fastened with each other by a separate fastening member, or provided integrally.

The first compound ring gear 546a and the second compound ring gear 546b may be provided in different shapes. For example, with respect to the rotation direction of the ring gear 546, each tooth of the first compound ring gear 546a may have a steeper slope in a first direction than a slope in a second direction opposite to the first direction. Conversely, each tooth of the second compound ring gear 546b may have a gentler slope in the first direction than a slope in the second direction.

A compound stopper 550 includes a first stopper 552 and a second stopper 554. The first stopper 552 and the second stopper 554 may include teeth having shapes corresponding to the first compound ring gear 546a and the second compound ring gear 546b, respectively.

Through the foregoing structure, a force exerted by the stopper 550 to restrict the ring gear 546 may increase.

Figure 10:
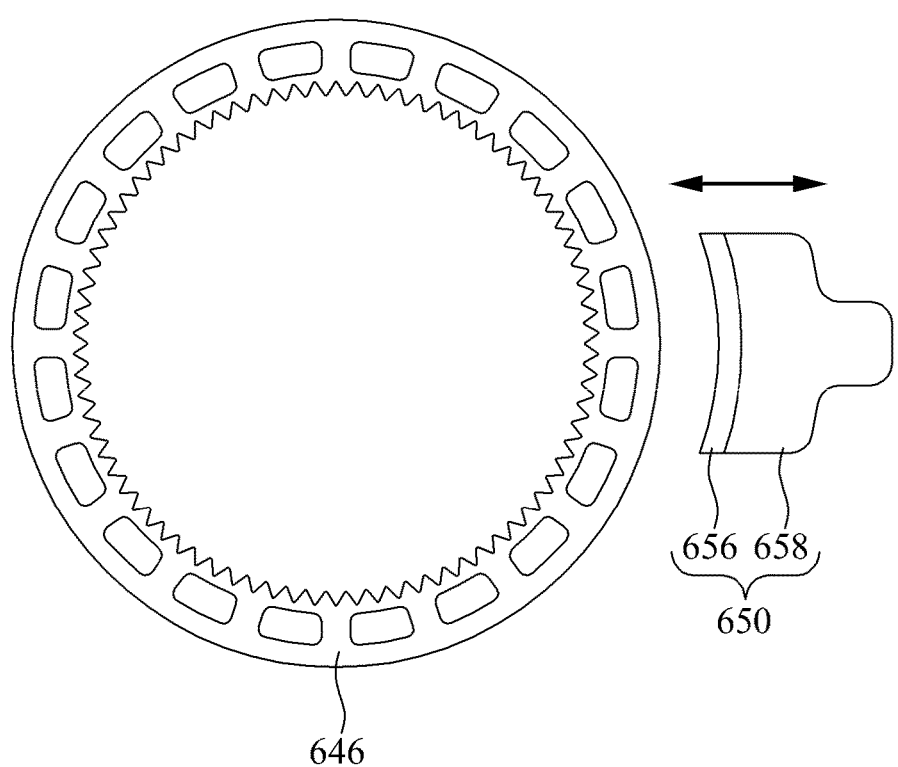
FIG. 10 is a view illustrating a ring gear and a stopper according to an example embodiment.

FIG. 10 is a view illustrating a ring gear and a stopper according to an example embodiment.

Referring to FIG. 10, a ring gear 646 may be restricted by a frictional force of a stopper 650.

For example, the stopper 650 may move forward and backward to selectively restrict the ring gear 646.

The stopper 650 includes a stopper body 658 and a brake pad 656. The brake pad 656 may include an elastic material, for example, rubber.

Figure 11:
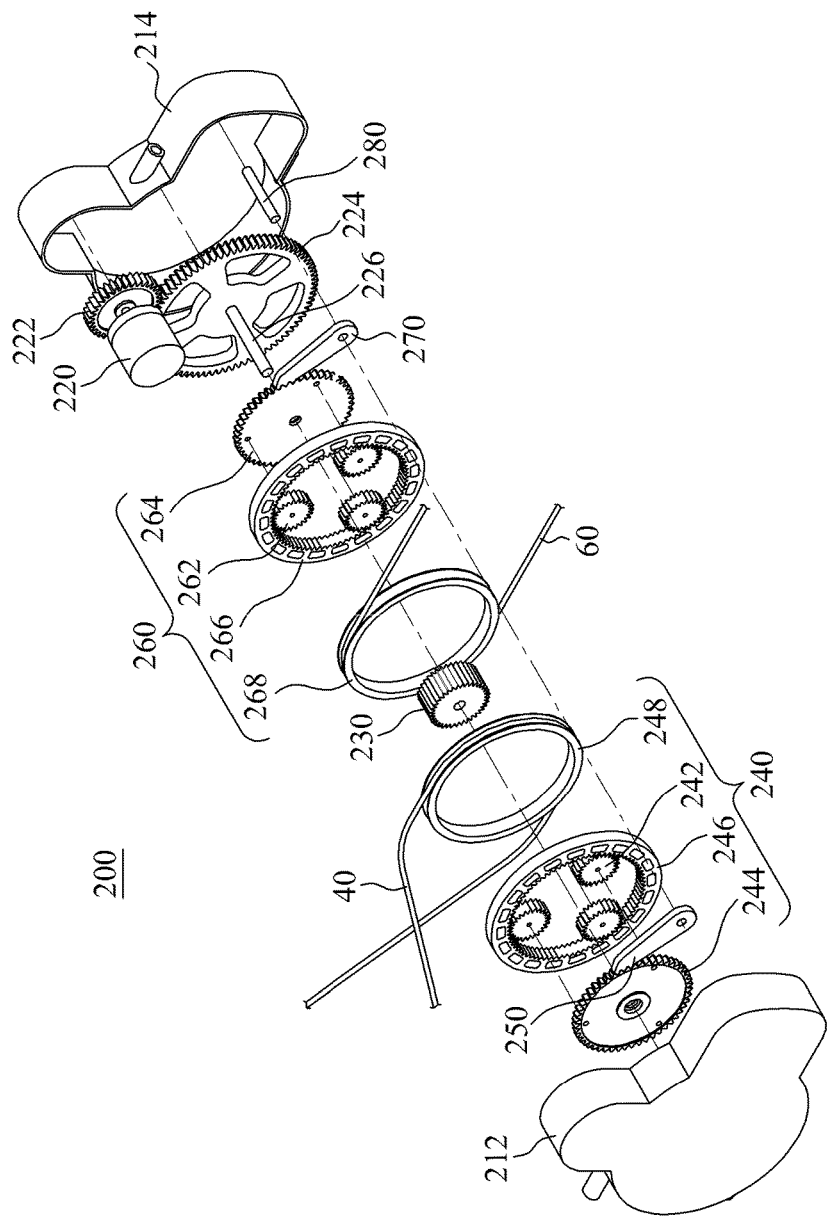
FIG. 11 is a front exploded perspective view illustrating a driving module according to an example embodiment.

FIG. 11 is a front exploded perspective view illustrating a driving module according to an example embodiment.

Duplicated descriptions provided with respect to the driving module 100 illustrated in FIG. 5 will be omitted for conciseness.

Referring to FIG. 11, a driving module 200 includes a first case 212, a second case 214, a driving source 220, a sun gear 230, a first decelerator 240, a first stopper 250, a second decelerator 260, a second stopper 270, and a stopper shaft 280.

The driving source 220 includes a driving gear 222, a decelerating gear 224, and a sun gear shaft 226.

The first decelerator 240 includes a first planet gear 242, a first carrier 244, a first ring gear 246, and a first pulley 248.

The first carrier 244 includes an outer surface to which the first stopper 250 can be engaged. For example, the outer surface of the first carrier 244 may include teeth.

The first pulley 248 may rotate using torque received from the first ring gear 246. A rotation velocity and a rotation direction of the first pulley 248 may be identical to a rotation velocity and a rotation direction of the first ring gear 246. The first pulley 248 and the first ring gear 246 may perform a single rigid body motion. For example, the first pulley 248 may be fastened with the first ring gear 246 by a separate fastening member, or the first pulley 248 and the first ring gear 246 may be provided as an integral body.

The first stopper 250 may enable the first carrier 244 to selectively rotate. The first stopper 250 may selectively restrict a movement of the first carrier 244. For example, the first stopper 250 may include teeth corresponding to the teeth provided on the outer surface of the first carrier 244.

A state in which the first stopper 250 is engaged to the first carrier 244 may be referred to as a "restriction state", and a state in which the first stopper 250 is separated from the first carrier 244 may be referred to as a "release state".

The first stopper 250 may rotate on the stopper shaft 280. According to a rotation angle of the first stopper 250, the first stopper 250 may enable the first carrier 244 to selectively rotate.

Similar to the first decelerator 240, the second decelerator 260 includes a second planet gear 262, a second carrier 264, a second ring gear 266, and a second pulley 268. Detailed descriptions of the second planet gear 262, the second carrier 264, the second ring gear 266, and the second pulley 268 will be omitted for conciseness. For example, the first decelerator 240 and the second decelerator 260 may be disposed in mirror images.

Similar to the first stopper 250, the second stopper 270 may enable the second carrier 264 to selectively rotate. A detailed description of the second stopper 270 will be omitted for conciseness.

Although the driving gear 222, the decelerating gear 224, the sun gear 230, the first planet gear 242, the second planet gear 262, the first carrier 244, the second carrier 264, the first ring gear 246, and the second ring gear 266 are illustrated as toothed gears, example embodiments are not limited thereto. The driving gear 222, the decelerating gear 224, the sun gear 230, the first planet gear 242, the second planet gear 262, the first carrier 244, the second carrier 264, the first ring gear 246, and the second ring gear 266 may be rotary bodies capable of transmitting power by rolling friction.

Figure 12:
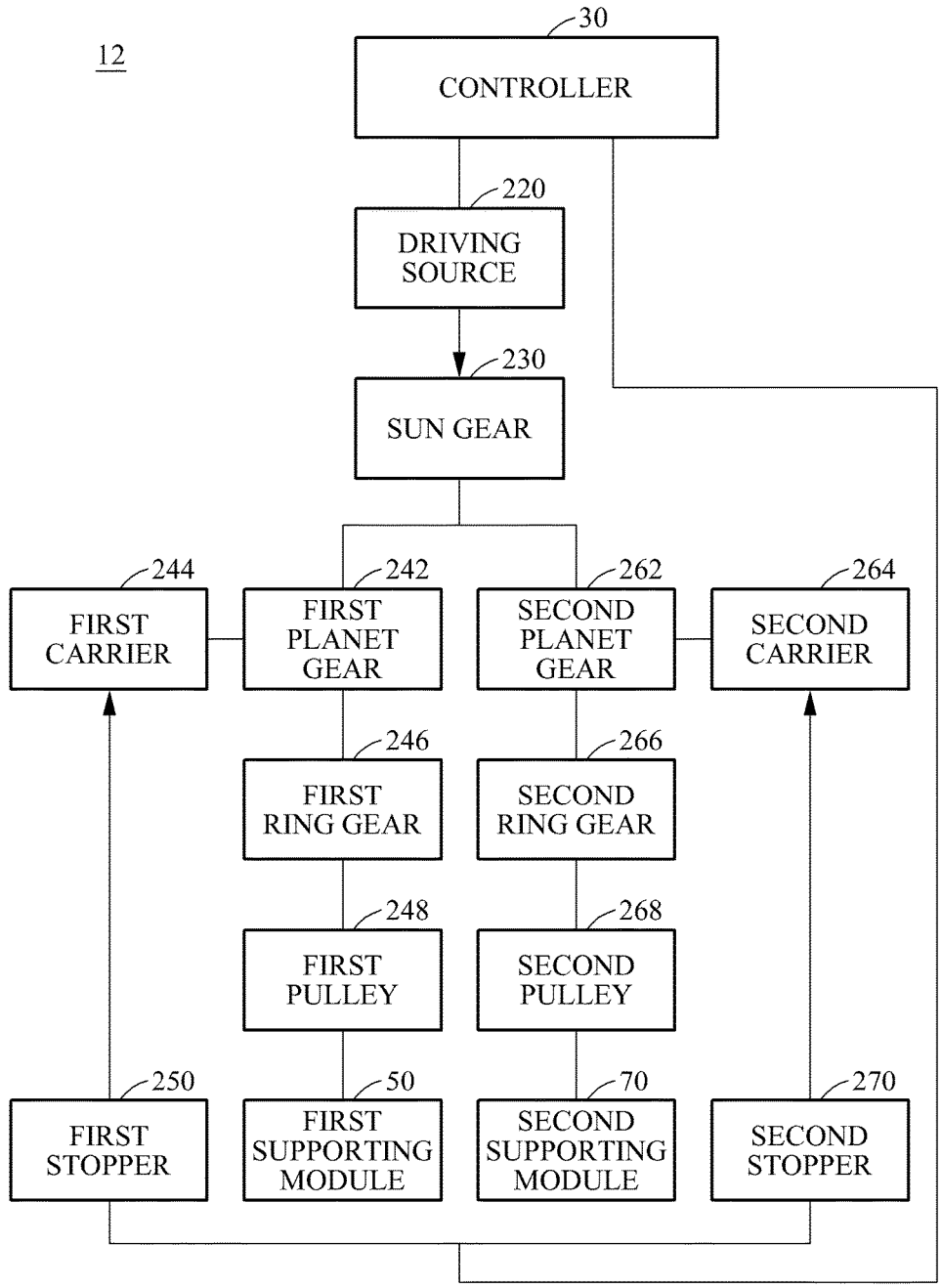
FIG. 12 is a block diagram illustrating a motion assistance apparatus according to an example embodiment.

FIG. 12 is a block diagram illustrating a motion assistance apparatus according to example embodiments.

Referring to FIG. 12, a motion assistance apparatus 12 may operate as follows.

A controller 30 may control (e.g., power on) the driving source 220 to transmit power to the sun gear 230. The controller 30 may operate the first stopper 250 and the second stopper 270 to be selectively connected to the first carrier 244 and the second carrier 264, respectively.

According to the operation of the first stopper 250, the first supporting module 50 may selectively rotate.

To operate the first supporting module 50, a force greater than a load applied to the first supporting module 50 is desired to be applied to the first supporting module 50. The load may be transmitted through the first power transmitting member 40 and the first pulley 248 to the first ring gear 246. Thus, a load greater than or equal to a threshold level exists in the first ring gear 246. Hereinafter, descriptions will be provided based on the foregoing premise.

When the first stopper 250 is connected to the first carrier 244, the first carrier 244 may be stopped. When power received from the sun gear 230 increases sufficiently, the first planet gear 242 may overcome a load applied to the first ring gear 246, and rotate. In response to the rotation of the first planet gear 242, the first ring gear 246 and the first pulley 248 may rotate. When the first pulley 248 rotates, the power may be transmitted through the first power transmitting member 40, and the first supporting module 50 may rotate.

When the first stopper 250 is separated from the first carrier 244, the first carrier 244 may be prepared to rotate. The first carrier 244 may be in an idling condition. The power received from the sun gear 230 may be transmitted through the first planet gear 242 to the first carrier 244 being in the idling condition, and the first carrier 244 may rotate. In this example, the first ring gear 246, the first pulley 248, the first power transmitting member 40, and the first supporting module 50 may not rotate.

Accordingly, the first supporting module 50 may selectively rotate based on the operation of the first stopper 250.

Similarly, the second supporting module 70 may selectively rotate based on the operation of the second stopper 270. Detailed descriptions will be omitted for conciseness.

By alternately connecting the first stopper 250 and the second stopper 270 to the first carrier 244 and the second carrier 264, respectively, the first supporting module 50 and the second supporting module 70 may alternately rotate. By alternately connecting the first stopper 250 and the second stopper 270 to the first carrier 244 and the second carrier 264, respectively, a walking motion of a user may be assisted.

Figure 13A:
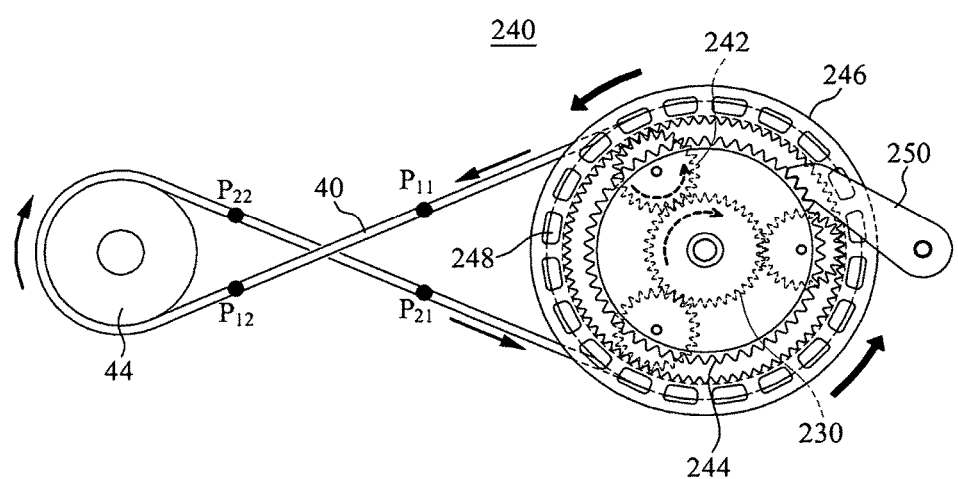
FIG. 13A illustrates an operation of a first decelerator associated with a forward movement of a first supporting module, viewed from a front of FIGS. 1, and 13B illustrates an operation of a first supporting module, viewed from a right side of FIG. 1, according to an example embodiment.
Figure 13B:
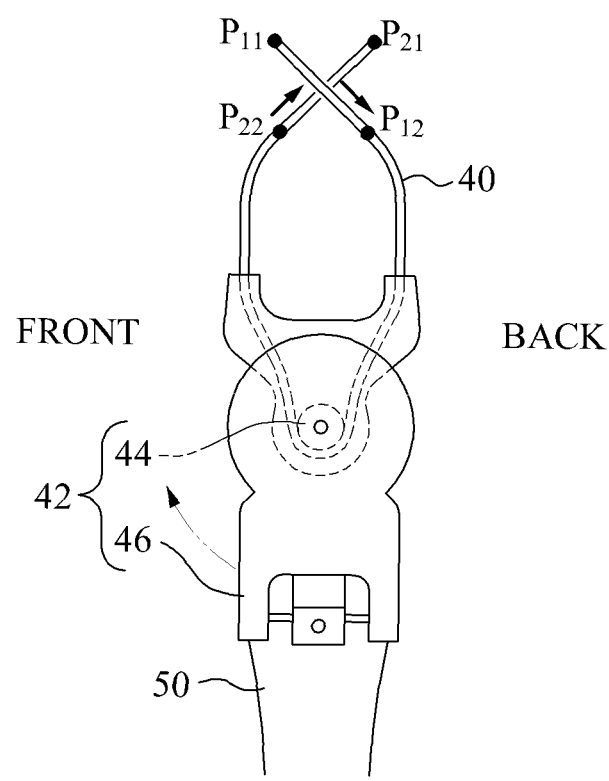

FIG. 13A illustrates an operation of the first decelerator 240 associated with a forward movement of the first supporting module 50, viewed from a front of FIG. 1, and FIG. 13B illustrates an operation of the first supporting module 240, viewed from a right side of FIG. 1, according to an example embodiment.

Figure 14A:
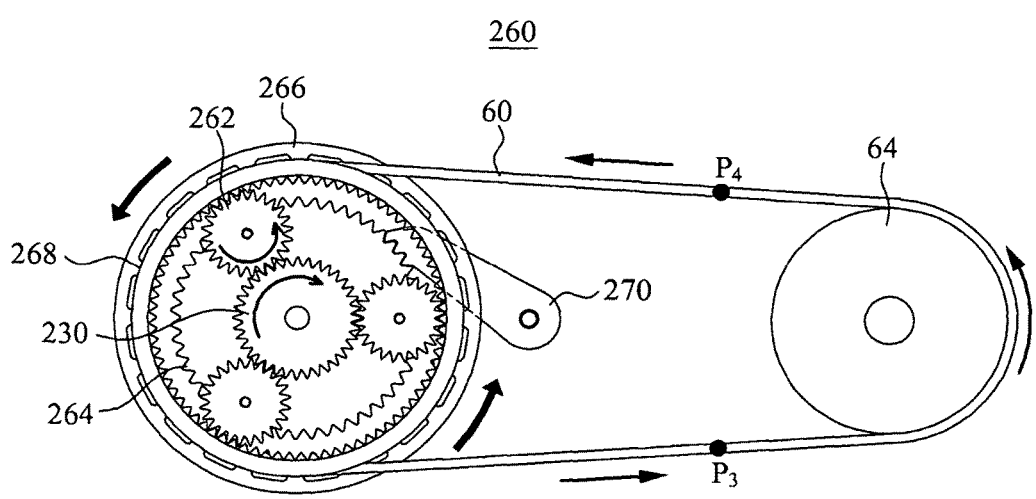
FIG. 14A illustrates an operation of a second decelerator associated with a forward movement of a second supporting module, viewed from the front of FIG. 1.
Figure 14B:
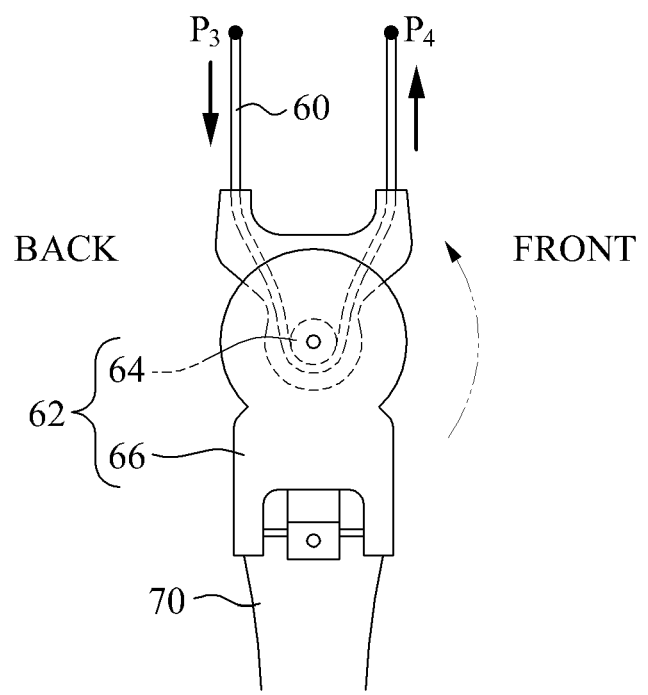
FIG. 14B illustrates a forward movement operation of a second supporting module, viewed from a left side of FIG. 1, according to an example embodiment.

FIG. 14A illustrates an operation of the second decelerator 260 associated with a forward movement of a second supporting module, viewed from the front of FIG. 1, and FIG. 14B illustrates forward movement operation of the second supporting module 70, viewed from a left side of FIG. 1, according to an example embodiment.

FIGS. 13A and 13B illustrate the first stopper 250 being connected to the first carrier 244, and FIGS. 14A and 14B illustrate the second stopper 270 being connected to the second carrier 264. Accordingly, the first carrier 244 and the second carrier 264 may be selectively stopped.

Referring to FIGS. 13A through 14B, when the sun gear 230 rotates in one direction, the first supporting module 50 and the second supporting module 70 may move forward.

For example, when the sun gear 230 rotates clockwise with respect to the front of FIG. 1, the first planet gear 242 and the second planet gear 262 may rotate counterclockwise, the first ring gear 246 and the second ring gear 266 may rotate counterclockwise, and the first pulley 248 and the second pulley 268 may rotate counterclockwise.

Referring to FIGS. 13A and 13B, the first power transmitting member 40, which is provided in an overlapping manner, when seeing from a side of the motion assistance apparatus 10, between the first pulley 248 and the first joint member 44 and includes a first portion and a second portion crossing the first portion, may enable the first joint member 44 to rotate in a direction opposite to the rotation direction of the first pulley 248. The first joint member 44 may be disposed on a right leg of a user. For example, the first joint member 44 may be disposed so that a surface of the first joint member 44, shown in FIG. 13A, may face a right side surface of the right leg of the user. Thus, the first joint member 44 may enable the first supporting module 50 to move forward.

As shown in FIGS. 14A and 14B, the second power transmitting member 40, which includes a first portion and a second portion not crossing the first portion and provided in a non-overlapping manner, when seeing from a side of the motion assistance apparatus 10, between the second pulley 268 and the second joint member 64 may enable the second joint member 64 to rotate in a direction identical to the rotation direction of the second pulley 268. The second joint member 64 may be disposed on a left leg of the user. For example, the second joint member 64 may be disposed so that a surface of the second joint member 64, shown in FIG. 8A, may face a left side surface of the left leg of the user. In this example, the second joint member 64 may enable the second supporting module 70 to move forward.

When the sun gear 230 rotates in another direction (e.g., a direction opposite to the one direction), the first supporting module 50 and the second supporting module 70 may move backward. For example, when the sun gear 230 rotates clockwise with respect to the front of FIG. 1, the first supporting module 50 and the second supporting module 70 may move backward. Detailed descriptions will be omitted for conciseness.

Through the foregoing configuration, the first stopper 250 and the second stopper 270 may operate using various methods depending on states of the user. Similar to the first stopper 150 and the second stopper 170 of FIGS. 7A through 8B, a motion state may be classified into three motion states, and arranged as shown in Table 2. Detailed descriptions will be omitted for conciseness.

TABLE 2

| | Motion state | First stopper | Second stopper |
| --- | --- | --- | --- |
| | Sitting-down/Standing-up | Restriction | Restriction |
| Walking | First supporting module movement | Restriction | Release |
| | Second supporting module movement | Release | Restriction |
| | Free motion | Release | Release |

According to some example embodiments, a first decelerator and a second decelerator may operate independently. Thus, one of the first decelerator and the second decelerator may be configured as shown in FIGS. 5, 7A, and 7B, and the other of the first decelerator and the second decelerator may be configured as shown in FIGS. 11, 14A, and 14B. A first power transmitting member and a second power transmitting member may be symmetrically disposed to each other with respect to the driving module 100 or 200.

For example, the first decelerator may be configured as shown in FIGS. 5, 7A, and 7B, and the first power transmitting member may be disposed in a twisted manner. The second decelerator may be configured as shown in FIGS. 11, 14A, and 14B, and the second power transmitting member may be disposed in a non-twisted manner. In this example, a first stopper and a second stopper may be in a restriction state. When a sun gear rotates counterclockwise, a first supporting module and a second supporting module may move forward. Through the foregoing configuration, the first stopper and the second stopper may operate using various methods depending on a state of the user. Similarly, a motion state may also be classified into three motion states. Detailed descriptions will be omitted for conciseness.

Referring to FIGS. 1 through 14B, a sun gear, a first planet gear, a first ring gear, a first carrier, a second planet gear, a second ring gear, and a second carrier may be referred to as a "first rotary body", a "second rotary body", a "third rotary body", a "fourth rotary body", a "fifth rotary body", a "sixth rotary body", and a "seventh rotary body", respectively.

The second rotary body may be engaged with the first rotary body, and configured to rotate. The third rotary body may be engaged with the second rotary body, and configured to rotate. The fourth rotary body may be connected to an axis of rotation of the second rotary body, and configured to rotate when the second rotary body revolves around the first rotary body.

The fifth rotary body may be engaged with the first rotary body, and configured to rotate. The sixth rotary body may be engaged with the fifth rotary body, and configured to rotate. The seventh rotary body may be connected to an axis of rotation of the fifth rotary body, and configured to rotate when the fifth rotary body revolves around the first rotary body.

According to some example embodiments, the first stopper may be selectively connected to one of the third rotary body and the fourth rotary body, and the second stopper may be selectively connected to one of the sixth rotary body and the seventh rotary body.

Figure 15:
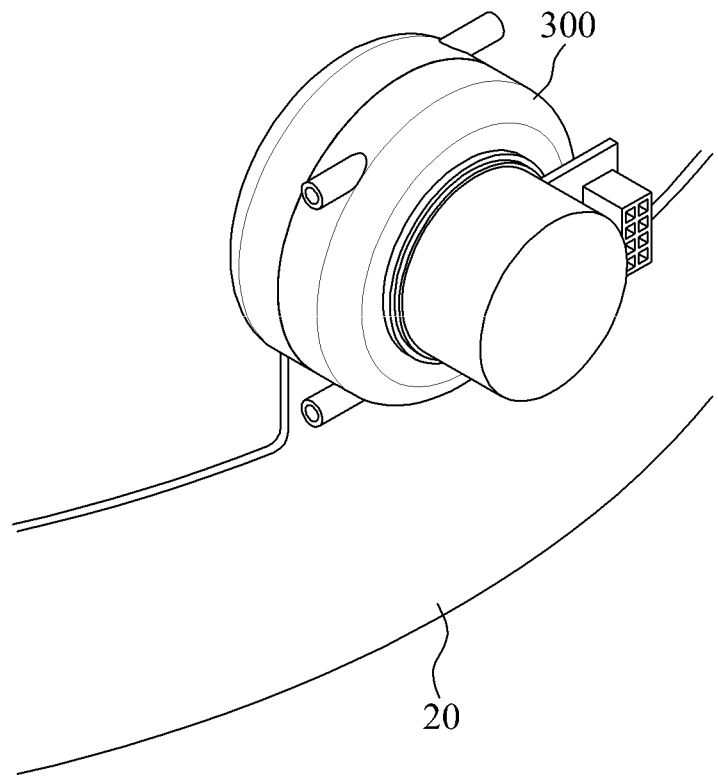
FIG. 15 is a rear perspective view illustrating a driving module according to an example embodiment.
Figure 16:
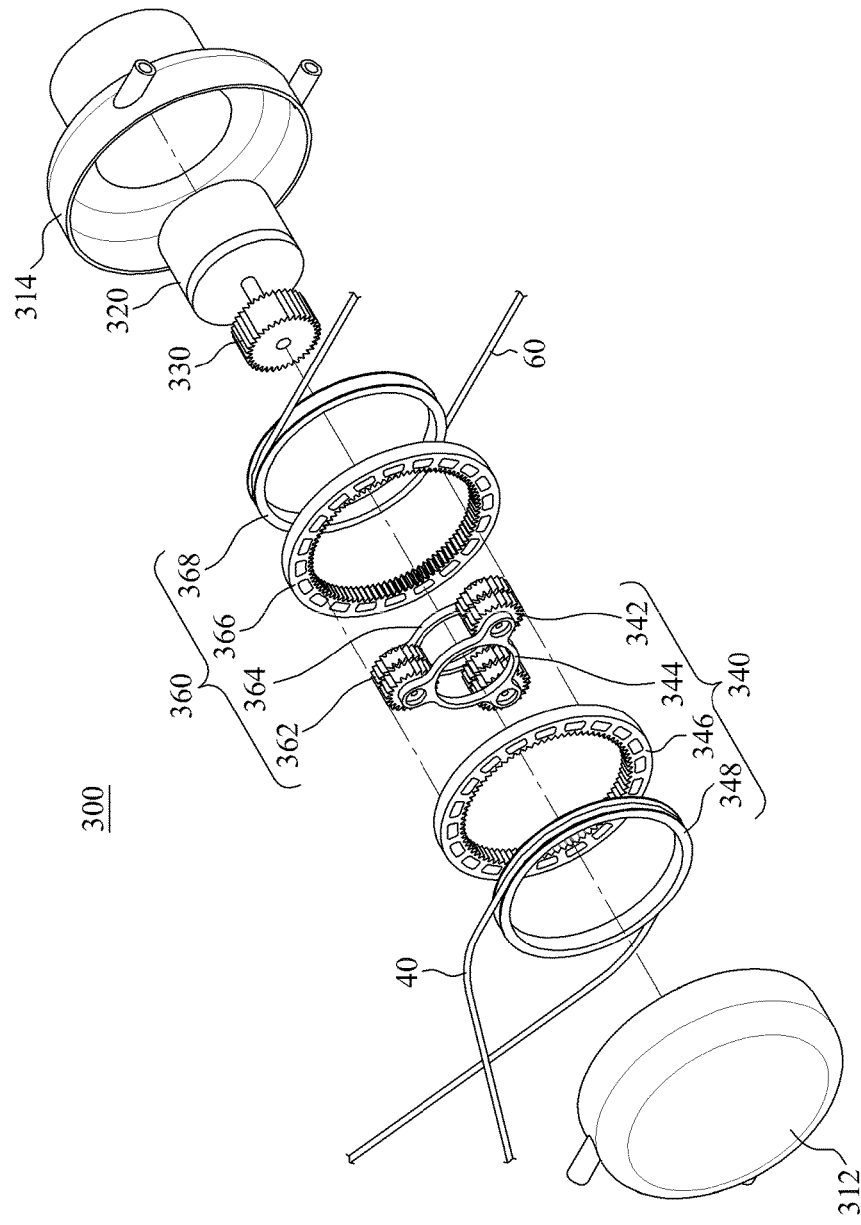
FIG. 16 is a front exploded perspective view illustrating a driving module according to an example embodiment.

FIG. 15 is a rear perspective view illustrating a driving module according to an example embodiment, and FIG. 16 is a front exploded perspective view illustrating a driving module according to an example embodiment.

Referring to FIGS. 15 and 16, a driving module 300 includes a first case 312, a second case 314, a driving source 320, a sun gear 330, a first decelerator 340, and a second decelerator 360.

The sun gear 330 may receive power from the driving source 320 and transmit the power to the first decelerator 340 and the second decelerator 360. For example, the sun gear 330 may be engaged with a first planet gear 342 and a second planet gear 362 simultaneously, thereby enabling the first planet gear 342 and the second planet gear 362 to rotate simultaneously. Thus, the first decelerator 340 including the first planet gear 342 as an input terminal may receive power from the sun gear 330. Similarly, the second decelerator 360 including the second planet gear 362 as an input terminal may receive power from the sun gear 330.

Although FIG. 16 illustrates the sun gear 330 including a single sun gear, the sun gear 330 may include a plurality of sun gears 330 configured to transmit power to the first decelerator 340 and the second decelerator 360. For example, the plurality of sun gears may perform a single rigid body motion. The first decelerator 340 includes the first planet gear 342, a first carrier 344, a first ring gear 346, and a first pulley 348.

The first pulley 348 may rotate using torque received from the first ring gear 346. A rotation velocity and a rotation direction of the first pulley 348 may be identical to a rotation velocity and a rotation direction of the first ring gear 346. The first pulley 348 and the first ring gear 346 may perform a single rigid body motion.

For example, the first pulley 348 may be fastened with the first ring gear 346 by a separate fastening member, or provided as an integral body with the first ring gear 346. For example, the first pulley 348 may be provided integrally on an outer circumferential surface of the first ring gear 346. In such a case, a groove may be provided on an outer circumferential surface of the first ring gear 346, and the first power transmitting member 40 may be wound along the groove.

Similar to the first decelerator 340, the second decelerator 360 may include the second planet gear 362, a second carrier 364, a second ring gear 366, and a second pulley 368. Detailed descriptions of the second planet gear 362, the second carrier 364, the second ring gear 366, and the second pulley 368 will be omitted for conciseness.

The first planet gear 342 and the second planet gear 362 may be coupled to have an identical axis of rotation. The first planet gear 342 and the second planet gear 362 may have identical revolution velocities with respect to the sun gear 330. The first planet gear 342 and the second planet gear 362 may perform a single rigid body motion. The first planet gear 342 and the second planet gear 362 may be fastened with each other by a separate fastening member, or may be provided as an integral body.

The first carrier 344 and the second carrier 364 may be connected to have an identical axis of rotation. The first carrier 344 and the second carrier 364 may have identical rotation directions and identical rotation velocities.

Because both the first carrier 344 and the second carrier 364 operate and function identically, one of the first carrier 344 and the second carrier 364 may be omitted. Further, the first carrier 344 and the second carrier 364 may be provided as an integral body.

A gear ratio from the sun gear 330 to an output terminal of the first decelerator 340 may be referred to as a "first gear ratio N1", and a gear ratio from the sun gear 330 to an output terminal of the second decelerator 360 may be referred to as a "second gear ratio N2."

In the present example embodiments, the first gear ratio N1 may be defined as a gear ratio from the sun gear 330 to the first ring gear 346. The second gear ratio N2 may be defined as a gear ratio from the sun gear 330 to the second ring gear 366.

The first gear ratio N1 may differ from the second gear ratio N2. Based on a difference between the first gear ratio N1 and the second gear ratio N2, the first decelerator 340 and the second decelerator 360 may perform relative motions with respect to each other.

According to some example embodiments, when a plurality of sun gears 330 is provided such that the number of teeth of a portion of the sun gears 330 are connected to the first decelerator 340 and the number of teeth of a remaining portion of the sun gears 330 are connected to the second decelerator 360, the first gear ratio N1 may be set to be different from the second gear ratio N2.

According to some example embodiments, by differently setting the number of teeth of the first planet gear 342 and the number of teeth of the second planet gear 362, and/or by differently setting the number of teeth of the first ring gear 346 and the number of teeth of the second ring gear 366, the first gear ratio N1 may be set to be different from the second gear ratio N2.

FIG. 16 illustrates a case in which a sun gear 330 includes a single gear, the number of teeth of the first planet gear 342 is equal to the number of teeth of the second planet gear 362, and the number of teeth of the first ring gear 346 is different from the number of teeth of the second ring gear 366. For example, the number of teeth of the first ring gear 346 may be smaller than the number of teeth of the second ring gear 366. For example, the first gear ratio N1 may be smaller than the second gear ratio N2. Hereinafter, descriptions will be provided based on the foregoing premise. However, other configurations in which the first gear ratio N1 differs from the second gear ratio N2 may also be possible.

Although the sun gear 330, the first planet gear 342, the second planet gear 362, the first ring gear 346, and the second ring gear 366 are illustrated as toothed gears, example embodiments are not limited thereto. The sun gear 330, the first planet gear 342, the second planet gear 362, the first ring gear 346, and the second ring gear 366 may be rotary bodies capable of transmitting power by rolling friction.

Figure 17:
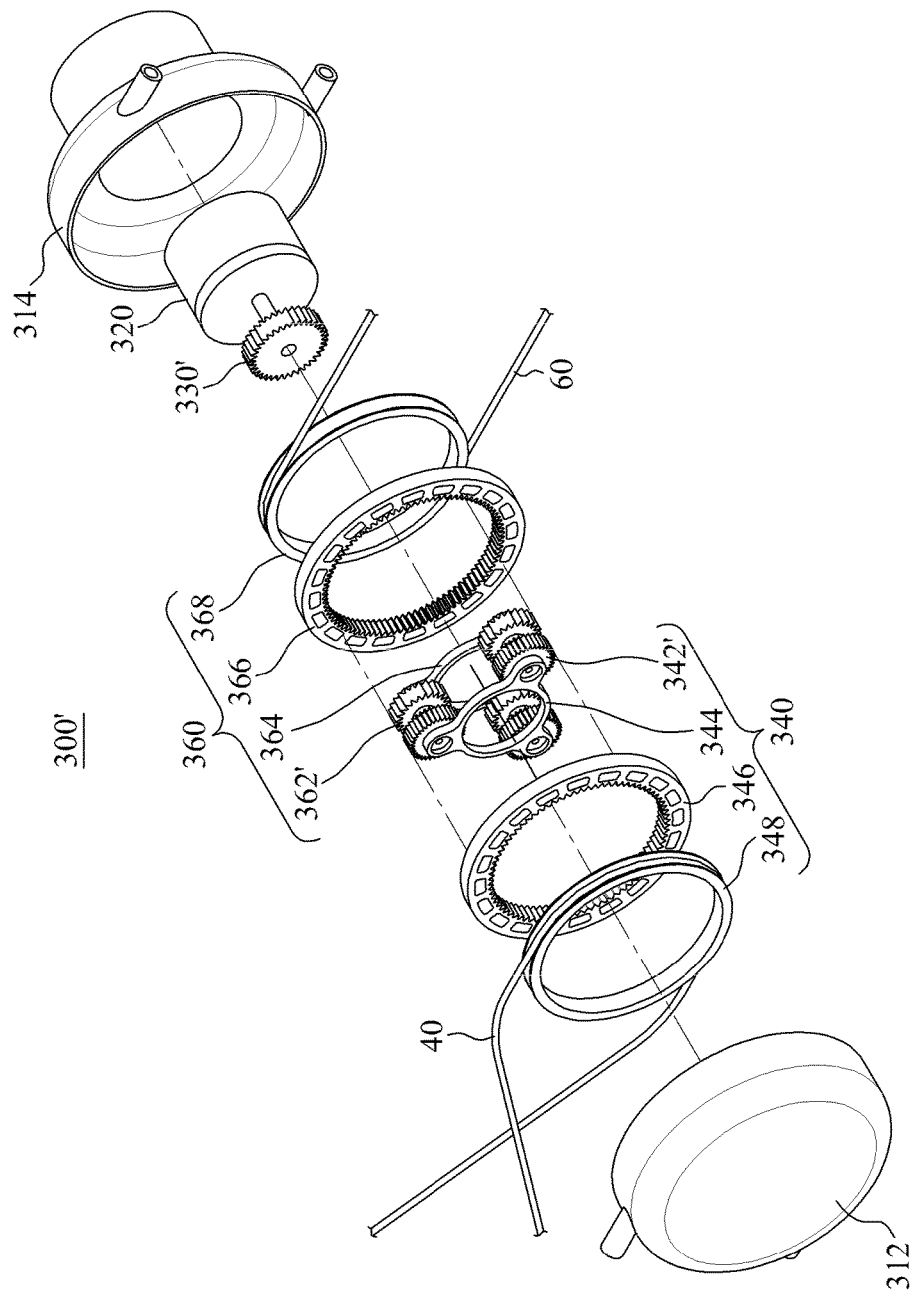
FIG. 17 is a front exploded perspective view illustrating a driving module according to an example embodiment.

FIG. 17 is a front exploded perspective view illustrating a driving module according to an example embodiment.

Referring to FIG. 17, a first planet gear 342' and a second planet gear 362' may be held together or provided as an integral body. In this example, a sun gear 330' may be connected to one of the first planet gear 342' and the second planet gear 362'. Further, the number of teeth of the first planet gear 342' may differ from the number of teeth of the second planet gear 362' and the sun gear 330' may be coupled to the second planet gear 362'.

The sun gear 330' may receive power from a driving source 320, and transmit the power to a first decelerator 340 and a second decelerator 360. For example, the sun gear 330' may transmit power to the second planet gear 362'. Thus, the second decelerator 360 including the second planet gear 362' as an input terminal may receive power from the sun gear 330'. When the second planet gear 362' rotates, the first planet gear 342' provided to be held together with the second planet gear 362' may also rotate. Thus, the first decelerator 340 including the first planet gear 342' as an input terminal may receive power from the sun gear 330'.

FIG. 18 is a block diagram illustrating a motion assistance apparatus according to an example embodiment.

Referring to FIG. 18, a motion assistance apparatus 13 may operate as follows.

A controller 30 may control (e.g., power on) a driving source 320 to transmit power to a sun gear 330. The power transmitted to the sun gear 330 may be transmitted to a first planet gear 342 and a second planet gear 362, simultaneously.

The first planet gear 342 may transmit power to a first carrier 344 and/or a first ring gear 346. The second planet gear 362 may transmit power to a second carrier 364 and/or a second ring gear 366.

Based on a difference between a first gear ratio N1 and a second gear ratio N2, the first ring gear 346 and the second ring gear 366 may perform relative motions with respect to each other. Thus, an angle between a first supporting module 50 and a second supporting module 70 may be adjusted.

The controller 30 may alternately change a rotation direction of the sun gear 330. Accordingly, the angle between the first supporting module 50 and the second supporting module 70 may alternately increase or decrease. Through the foregoing structure, a walking motion of a user may be assisted.

According to some example embodiments, the driving module 300 of FIG. 16 may operate while all of the first carrier 344, the second carrier 364, the first ring gear 346, and the second ring gear 366 are not being fixed to the first case 312 and the second case 314. In such case, the first carrier 344 and the second carrier 364 may not be restricted by a component other than axes of rotation of the first planet gear 342 and the second planet gear 362. Further, the first ring gear 346 and the second ring gear 366 may not be restricted by a component other than the first planet gear 342, the second planet gear 362, the first pulley 348, and the second pulley 368. A bearing may be provided to enable free rotation of a carrier or a ring gear.

Thus, absolute positions of the first carrier 344, the second carrier 364, the first ring gear 346, and the second ring gear 366 may not be determined based on a rotation angle of the sun gear 330. The absolute positions of the first carrier 344, the second carrier 364, the first ring gear 346, and the second ring gear 366 may change based on torque received from the sun gear 330 and a load received from outside. For example, a reference position may be determined based on a position of each leg while a user (e.g., a wearer) is walking.

The present example embodiment is provided to assist a walking motion of a user by adjusting the angle between the first supporting module 50 and the second supporting module 70. According to this example, although absolute positions of the first supporting module 50 and the second supporting module 70 cannot be determined, those skilled in the art may implement a motion assistance apparatus capable of adjusting the angle between the first supporting module 50 and the second supporting module 70.

Thus, through the relative motions of the first ring gear 346 and the second ring gear 366 with respect to each other, the angle between the first supporting module 50 and the second supporting module 70 may be adjusted. The absolute positions of the first supporting module 50 and the second supporting module 70 may change based on the load received from outside and the sun gear 330.

FIG. 19 is a block diagram illustrating a motion assistance apparatus according to an example embodiment.

Referring to FIG. 19, a motion assistance apparatus 13' may operate as follows.

Power transmitted to a sun gear 330' may be transmitted one of a first planet gear 342' and a second planet gear 362'. For example, the power transmitted to the sun gear 330' may be transmitted to the second planet gear 362'. When the second planet gear 362' rotates, the first planet gear 342' provided to be held together or as an integral body with the second planet gear 362' may rotate.

The first planet gear 342' may transmit power to a first carrier 344 and/or a first ring gear 346. The second planet gear 362' may transmit power to a second carrier 364 and/or a second ring gear 366.

Based on a difference between a first gear ratio N1 and a second gear ratio N2, the first ring gear 346 and the second ring gear 366 may perform relative motions with respect to each other. Thus, an angle between a first supporting module 50 and a second supporting module 70 may be adjusted.

The controller 30 may alternately change a rotation direction of the sun gear 330'. In this example, the angle between the first supporting module 50 and the second supporting module 70 may alternately increase or decrease. Through the foregoing structure, a walking motion of a user may be assisted.

Figure 20A:
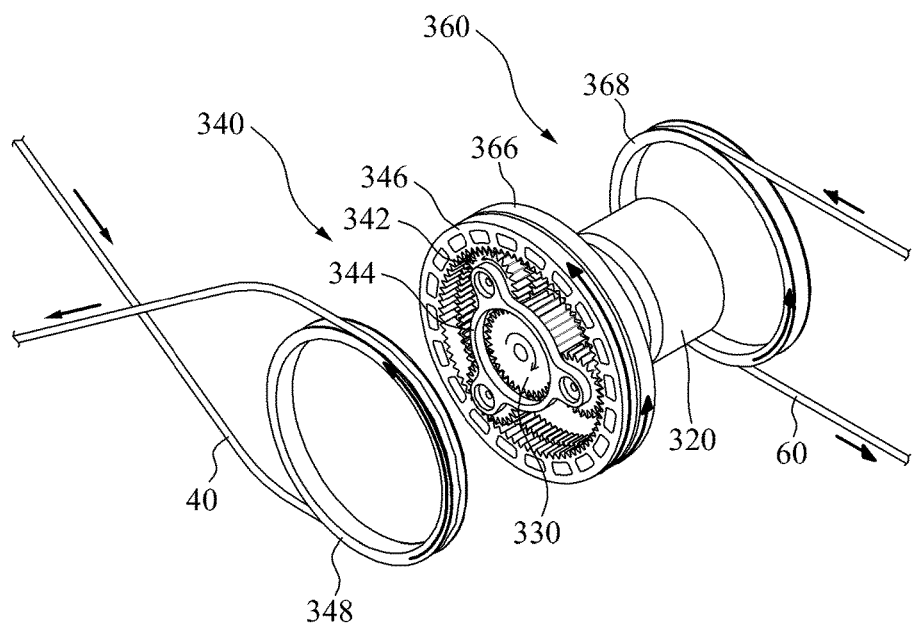
FIGS. 20A and 20B are views illustrating operations of a driving module, a first supporting module, and a second supporting module when a first carrier and a second carrier are fixed to each other according to an example embodiment.
Figure 20B:
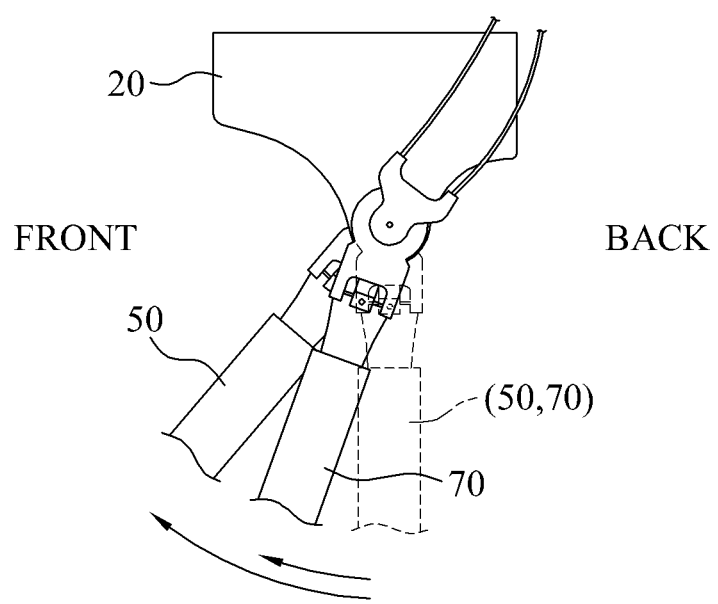

FIGS. 20A and 20B are views illustrating operations of the driving module 300 of FIG. 16, the first supporting module 50, and the second supporting module 70 when the first carrier 344 and the second carrier 364 are fixed to each other according to an example embodiment. In particular, FIG. 20A illustrates operations of the first decelerator 340 and the second decelerator 360, and FIG. 20B illustrates operations of the first supporting module 50 and the second supporting module 70.

Although the first carrier 344 and the second carrier 364 do not have to be fixed to each other in the present example embodiments, a case in which the first carrier 344 and the second carrier 364 are fixed to each other will be described first for ease of understanding.

Referring to FIG. 20A, when the sun gear 330 rotates clockwise, the first planet gear 342 and the second planet gear 362 may rotate counterclockwise, and a first ring gear 346 and a second ring gear 366 may rotate counterclockwise.

When the number of teeth of the first ring gear 346 is smaller than the number of teeth of the second ring gear 366, a first gear ratio N1 may be smaller than a second gear ratio N2. Thus, the first ring gear 346 may rotate at a faster angular velocity than the second ring gear 366. The first ring gear 346 and the second ring gear 366 may have different angular velocities. Accordingly, the first pulley 348 and the second pulley 368 may have different angular velocities.

Thus, as shown in FIG. 20B, an angle between the first supporting module 50 and the second supporting module 70 may increase. The first supporting module 50 and the second supporting module 70 may move forward.

Conversely, when the sun gear 330 rotates counterclockwise, the first supporting module 50 and the second supporting module 70 may move backward.

In a state as shown in FIG. 20B, a user may apply a load to at least one of the first decelerator 340 and the second decelerator 360 to lift an upper body of the user for upright walking. Hereinafter, descriptions will be provided with reference to FIGS. 21A and 21B.

Figure 21A:
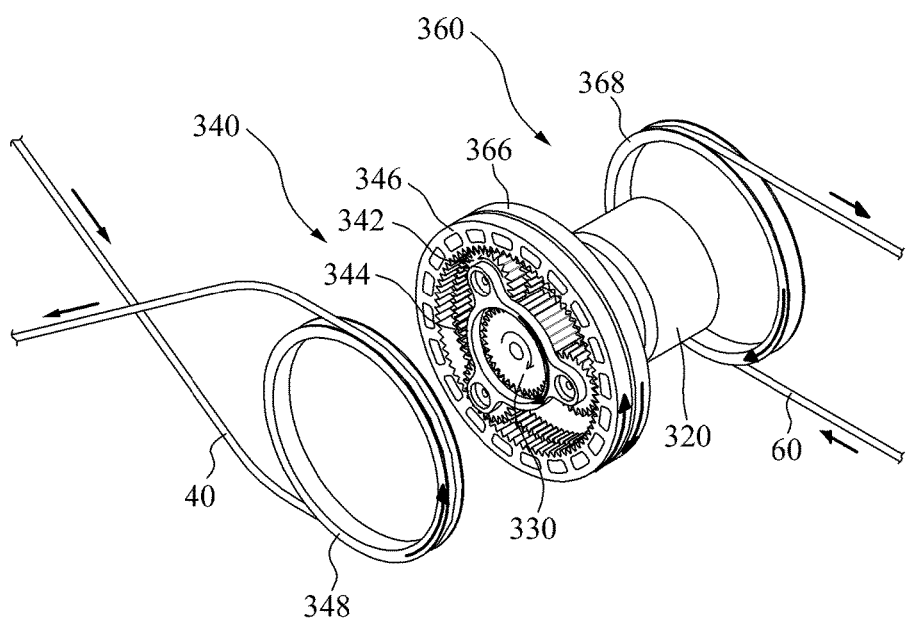
FIGS. 21A and 21B are views illustrating operations of a driving module, a first supporting module, and a second supporting module when power of a driving source is applied according to an example embodiment.
Figure 21B:
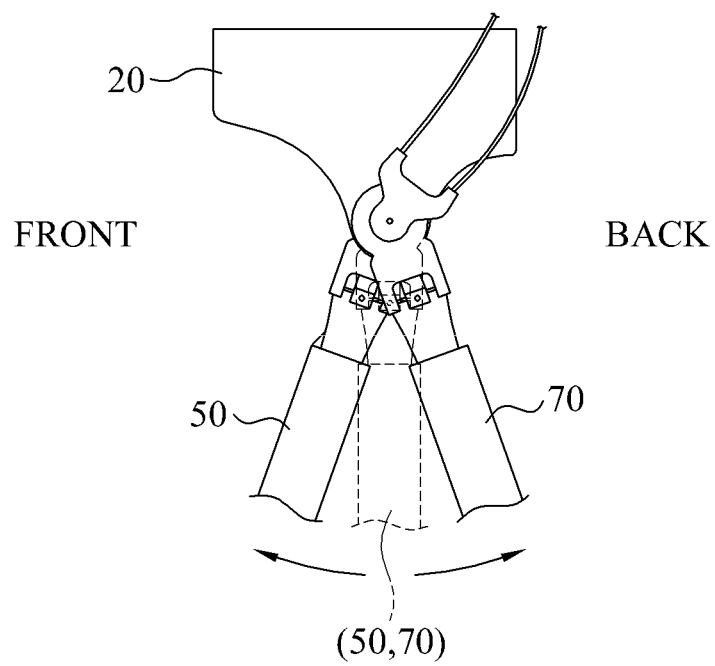

FIGS. 21A and 21B are views illustrating operations of the driving module 300 of FIG. 16, the first supporting module 50, and the second supporting module 70 when power of the driving source 320 is applied according to an example embodiment. In particular, FIG. 21A illustrates operations of the first decelerator 340 and the second decelerator 360, and FIG. 21B illustrates operations of the first supporting module 50 and the second supporting module 70.

Referring to FIGS. 21A, and 21B when a user applies a load to the first decelerator 340 and the second decelerator 360 to lift an upper body of the user in a state in which power of the driving source 320 is applied, the first carrier 344 and the second carrier 364 may rotate such that the first supporting module 50 moves backward and the second supporting module 70 moves forward.

When the user walks upright, the first carrier 344 and the second carrier 364 may rotate so that a rotation direction of the first ring gear 346 may be opposite to a rotation direction of the second ring gear 366. Thus, the first pulley 348 connected to the first ring gear 346 and the second pulley 368 connected to the second ring gear 366 may rotate in opposite directions.

Thus, when the sun gear 330 rotates clockwise, the first supporting module 50 may move forward, and the second supporting module 70 may move backward, as shown in FIG. 21B.

Conversely, when the sun gear 330 rotates counterclockwise, the first supporting module 50 may move backward, and the second supporting module 70 may move forward.

The controller 30 of FIG. 18 may alternately change a rotation direction of the sun gear 330, thereby assisting a walking motion of the user.

Figure 22A:
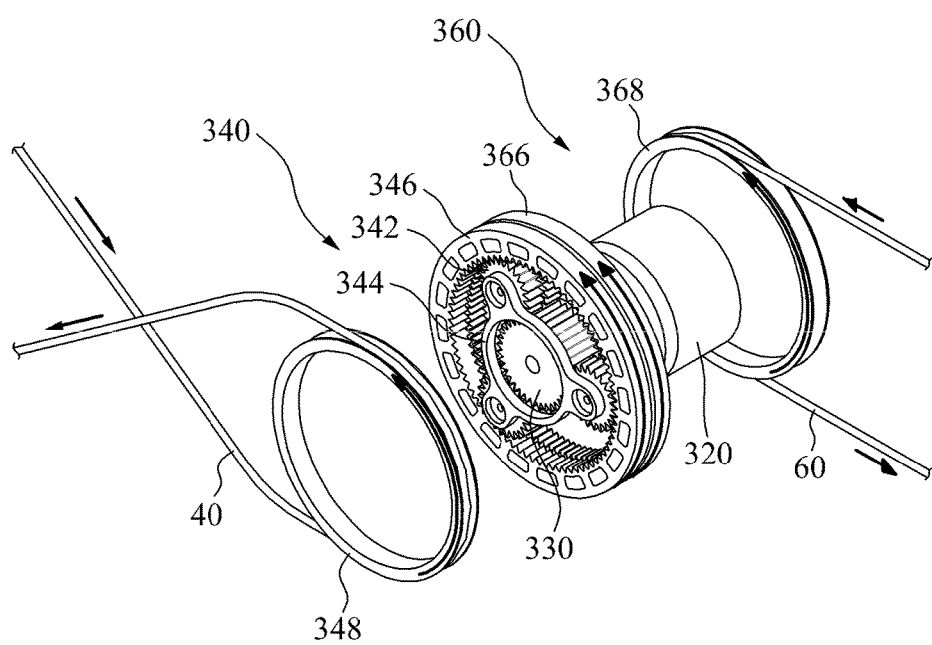
FIGS. 22A and 22B are views illustrating operations of a driving module, a first supporting module, and a second supporting module when power of a driving source is blocked according to an example embodiment.
Figure 22B:
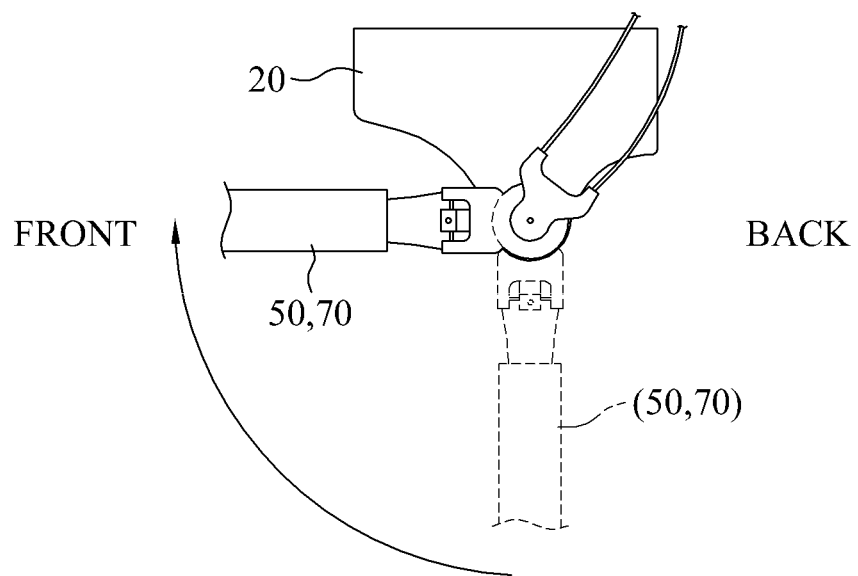

FIGS. 22A and 22B are views illustrating operations of the driving module 300 of FIG. 16, the first supporting module 50, and the second supporting module 70 when power of the driving source 320 is blocked according to an example embodiment. In particular, FIG. 22A illustrates operations of the first decelerator 340 and the second decelerator 360, and FIG. 22B illustrates operations of the first supporting module 50 and the second supporting module 70.

Referring to FIG. 22A, when a user applies a load for bending an upper body of the user to the first decelerator 340 and the second decelerator 360 in a state in which the driving source 320 is powered off, the first supporting module 50 and the second supporting module 70 may transmit loads of identical directions to the first pulley 348 and the second pulley 368.

In this example, the first ring gear 346, the second ring gear 366, the first planet gear 342, the second planet gear 362, the first carrier 344, the second carrier 364, and the sun gear 330 may perform a single rigid body motion. The first ring gear 346, the second ring gear 366, the first planet gear 342, the second planet gear 362, the first carrier 344, the second carrier 364, and the sun gear 330 may have identical rotation velocities.

Thus, as shown in FIG. 22B, the user may freely perform a sitting-down motion without receiving the load by the driving source 320.

Conversely, when the user applies a load for lifting the upper body of the user to the first decelerator 340 and the second decelerator 360 in a state in which the driving source 320 is powered off, the user may freely perform a standing-up motion without receiving the load by the driving source 320.

The user may apply a load for bending the upper body of the user to the first decelerator 340 and the second decelerator 360 in a state in which the driving source 320 is held. For example, because the sun gear 330 is fixed, the first ring gear 346 and the second ring gear 366 may rotate at different angular velocities with respect to the sun gear 330. Further, as shown in FIG. 20B, the first supporting module 50 and the second supporting module 70 may move in identical directions to be spaced apart from each other. Through the foregoing process, the user may perform the sitting-down motion.

In this example, by enabling a ratio of a third gear ratio N3 between the first pulley 348 and the first joint assembly 42 to a fourth gear ratio N4 between the second pulley 368 and the second joint assembly 62 to be equal to an inverse number of a ratio of a first gear ratio N1 to a second gear ratio N2, the first supporting module 50 and the second supporting module 70 may be mitigated or prevented from being spaced apart from each other while the user is sitting down.

As another method, by reducing a difference between the first gear ratio N1 and the second gear ratio N2, an angle at which the first supporting module 50 and the second supporting module 70 are to be spaced apart from each other while the user is sitting down may be reduced. Thus, even when the difference between the first gear ratio N1 and the second gear ratio N2 is relatively small, the first supporting module 50 and the second supporting module 70 may secure an angular velocity sufficient for a walking motion using the driving source 320 having a high revolution per minute (RPM) value.

The three motion states described above may be arranged as shown in Table 3.

TABLE 3

| | Motion state | Driving source/Sun Gear |
|---|---|---|
| Walking | First supporting module forward/Second supporting module backward | ON/Clockwise |
| | First supporting module backward/Second supporting module forward | ON/Counterclockwise |
| | Sitting-down/Standing-up | (i) OFF/Not holding or not engaging the driving source (ii) ON/Holding or engaging the driving source |

Figure 23:
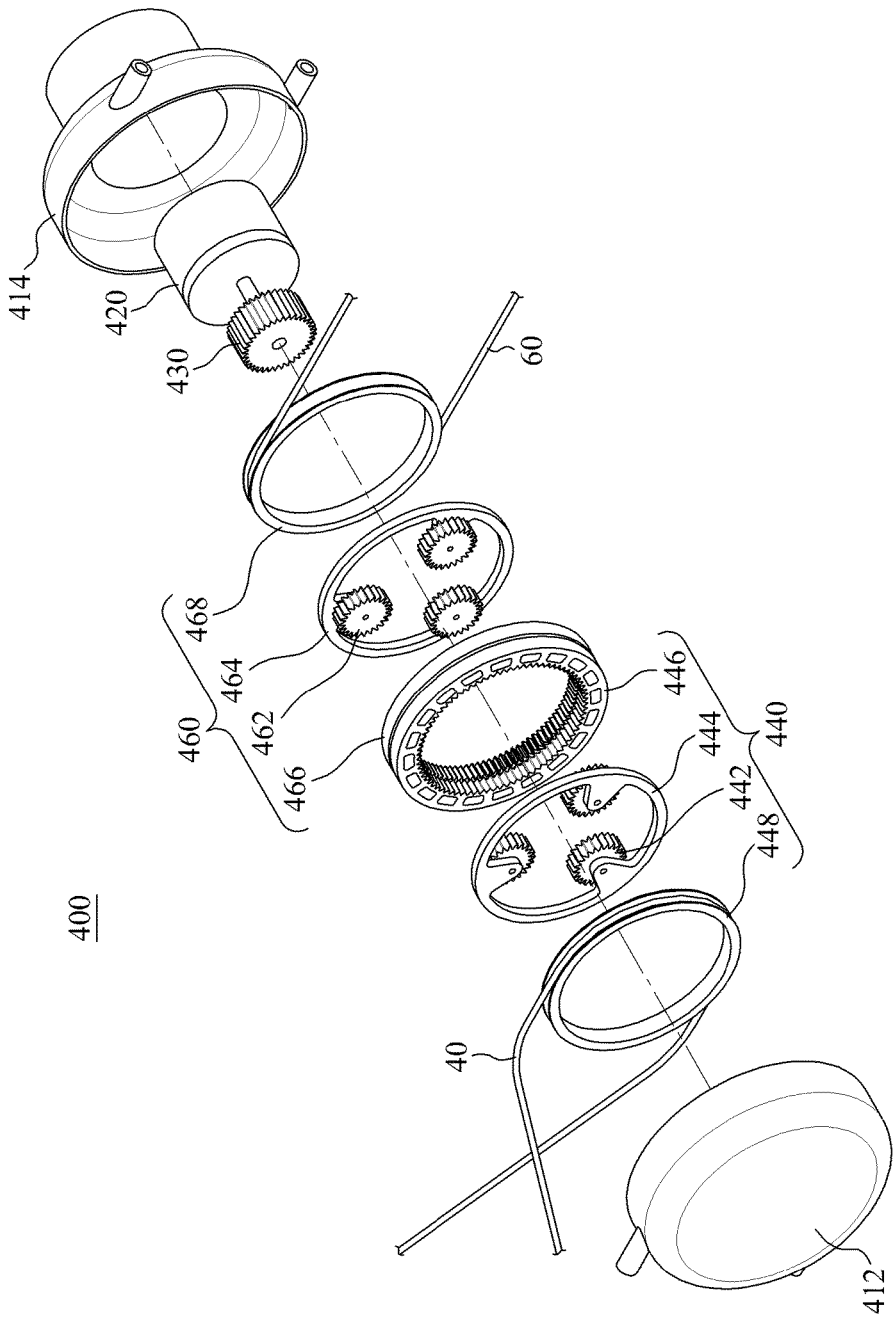
FIG. 23 is a front exploded perspective view illustrating a driving module according to an example embodiment.

FIG. 23 is a front exploded perspective view illustrating a driving module according to example embodiments. Duplicated descriptions provided with respect to the driving module 300 of FIG. 16 will be omitted for conciseness.

Referring to FIG. 23, a driving module 400 includes a first case 412, a second case 414, a driving source 420, a sun gear 430, a first decelerator 440, and a second decelerator 460.

The sun gear 430 may receive power from the driving source 420, and transmit the power to the first decelerator 440 and the second decelerator 460. For example, the sun gear 430 may be engaged with a first planet gear 442 and a second planet gear 462 simultaneously, thereby enabling the first planet gear 442 and the second planet gear 462 to rotate simultaneously. Thus, the first decelerator 440 including the first planet gear 442 as an input terminal may receive power from the sun gear 430. Similarly, the second decelerator 460 including the second planet gear 462 as an input terminal may receive power from the sun gear 430.

The first decelerator 440 includes the first planet gear 442, a first carrier 444, a first ring gear 446, and a first pulley 448.

The first pulley 448 may rotate using torque received from the first carrier 444. A rotation velocity and a rotation direction of the first pulley 448 may be identical to a rotation velocity and a rotation direction of the first carrier 444. The first pulley 448 and the first carrier 444 may perform a single rigid body motion.

For example, the first pulley 448 may be fastened with the first carrier 444 by a separating fastening member, or provided as an integral body with the first carrier 444. For example, the first pulley 448 may be provided integrally on an outer circumferential surface of the first carrier 444. A groove may be provided on the outer circumferential surface of the first carrier 444, and the first power transmitting member 40 may be wound along the groove. Through the foregoing structure, the number of components may be reduced, and a manufacturing cost and time may be saved.

Similar to the first decelerator 440, the second decelerator 460 may include the second planet gear 462, a second carrier 464, a second ring gear 466, and a second pulley 468. Detailed descriptions of the second planet gear 462, the second carrier 464, the second ring gear 466, and the second pulley 468 will be omitted for conciseness.

The first ring gear 446 and the second ring gear 466 may have identical rotation velocities. The first ring gear 446 and the second ring gear 466 may be fastened with each other by a separate fastening member, or provided as an integral body.

In the present example embodiments, the first carrier 344 and the second carrier 364 may be provided as separate members.

A gear ratio from the sun gear 430 to an output terminal of the first decelerator 440 may be referred to as a "first gear ratio N1", and a gear ratio from the sun gear 430 to an output terminal of the second decelerator 460 may be referred to as a "second gear ratio N2."

In the present example embodiments, the first gear ratio N1 may be defined as a gear ratio from the sun gear 430 to the first carrier 444. The second gear ratio N2 may be defined as a gear ratio from the sun gear 430 to the second carrier 464.

The first gear ratio N1 may differ from the second gear ratio N2. Based on a difference between the first gear ratio N1 and the second gear ratio N2, the first decelerator 440 and the second decelerator 460 may perform relative motions with respect to each other. Detailed descriptions will be omitted for conciseness.

FIG. 23 illustrates a case in which the sun gear 430 includes a single sun gear, the number of teeth of the first planet gear 442 is equal to the number of teeth of the second planet gear 462, and the number of teeth of the first ring gear 446 is different from the number of teeth of the second ring gear 466. For example, the number of teeth of the first ring gear 446 may be smaller than the number of teeth of the second ring gear 466. In this example, the first gear ratio N1 may be smaller than the second gear ratio N2. Hereinafter, descriptions will be provided based on the foregoing premise. However, other configurations in which the first gear ratio N1 differs from the second gear ratio N2 may also be possible.

Although the sun gear 430, the first planet gear 442, the second planet gear 462, the first ring gear 446, and the second ring gear 466 are illustrated as toothed gears, example embodiments are not limited thereto. The sun gear 430, the first planet gear 442, the second planet gear 462, the first ring gear 446, and the second ring gear 466 may be rotary bodies capable of transmitting power by rolling friction.

Figure 24:
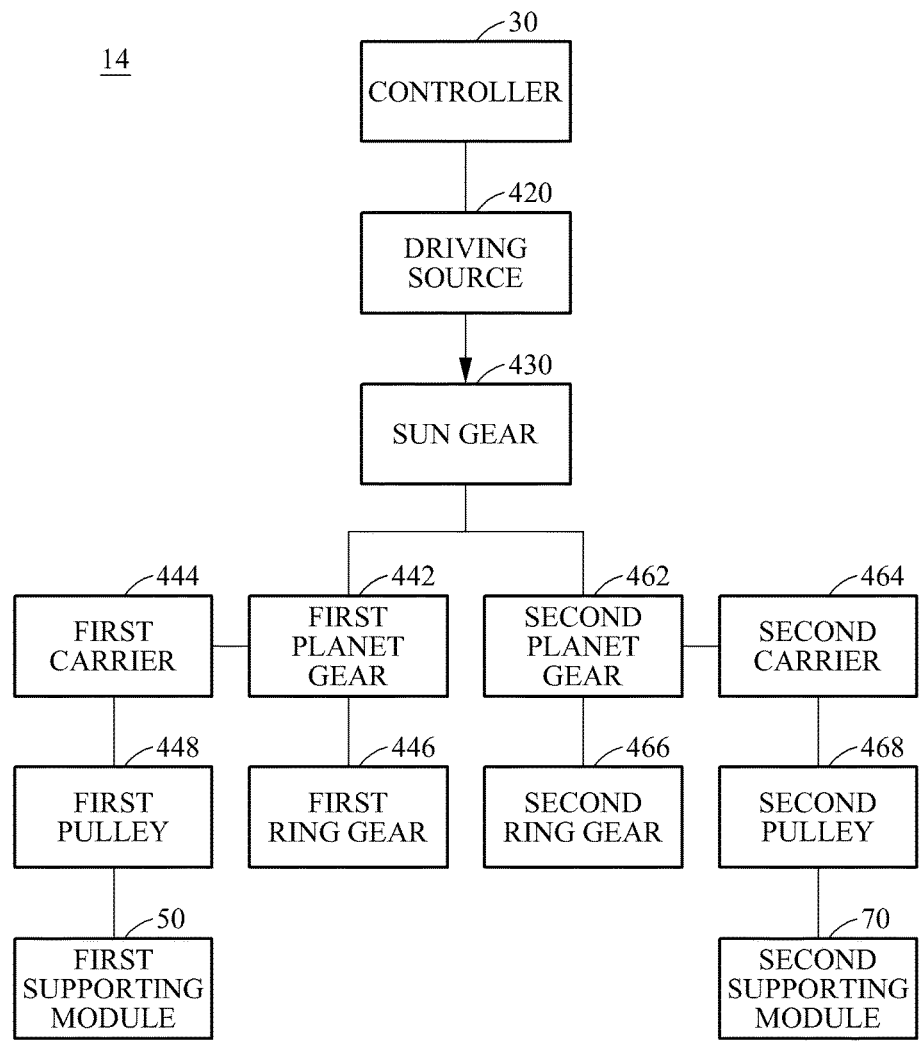
FIG. 24 is a block diagram illustrating a motion assistance apparatus according to an example embodiment.

FIG. 24 is a block diagram illustrating a motion assistance apparatus according to an example embodiment.

Referring to FIG. 24, a motion assistance apparatus 14 may operate as follows.

A controller 30 may control (e.g., power on) the driving source 420 to transmit power to the sun gear 430. The power transmitted to the sun gear 430 may be transmitted to the first planet gear 442 and the second planet gear 462, simultaneously.

The first planet gear 442 may transmit power to the first carrier 444 and/or the first ring gear 446. The second planet gear 462 may transmit power to the second carrier 464 and/or the second ring gear 466.

Based on a difference between a first gear ratio N1 and a second gear ratio N2, the first carrier 444 and the second carrier 464 may perform relative motions with respect to each other. Thus, an angle between the first supporting module 50 and the second supporting module 70 may be adjusted.

The controller 30 may alternately change a rotation direction of the sun gear 430. In this example, the angle between the first supporting module 50 and the second supporting module 70 may alternately increase or decrease. Through the foregoing structure, a walking motion of a user may be assisted.

According to some example embodiments, the driving module 400 of FIG. 23 may operate while all of the first carrier 444, the second carrier 464, the first ring gear 446, and the second ring gear 466 are not being fixed to the first case 412 and the second case 414. In such cases, the first carrier 444 and the second carrier 464 may not be restricted by a component other than axes of rotation of the first planet gear 442 and the second planet gear 462, the first pulley 448, and the second pulley 468. Further, the first ring gear 446 and the second ring gear 466 may not be restricted by a component other than the first planet gear 442, the second planet gear 462. A bearing may be provided to enable free rotation of a carrier or a ring gear.

Thus, through the relative motions of the first carrier 444 and the second carrier 464 with respect to each other, the angle between the first supporting module 50 and the second supporting module 70 may be adjusted. Absolute positions of the first supporting module 50 and the second supporting module 70 may change based on a load received from outside and the sun gear 430.

Figure 25A:
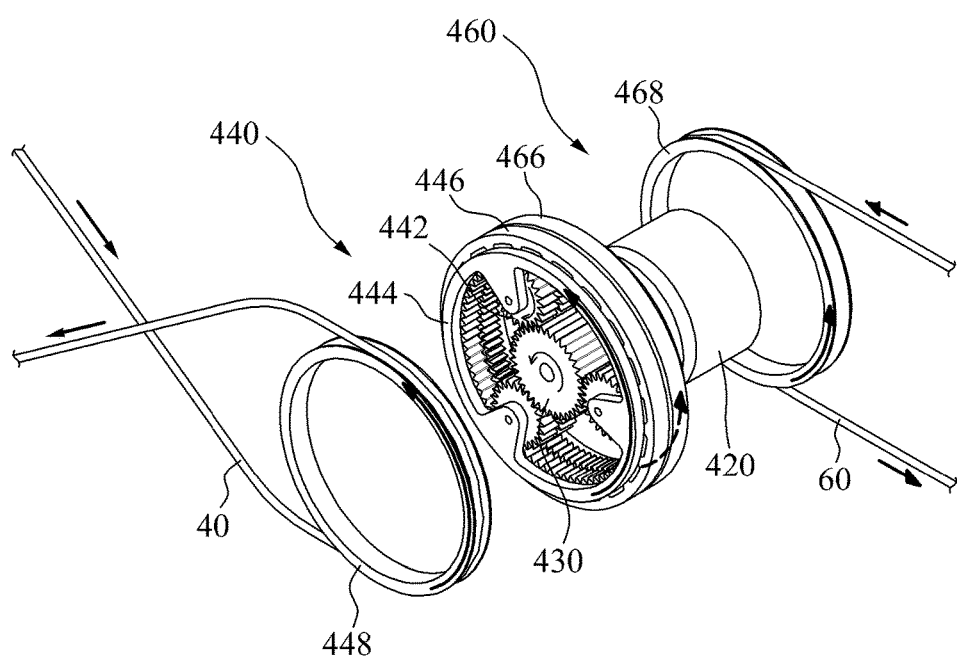
FIGS. 25A and 25B are views illustrating operations of a driving module, a first supporting module, and a second supporting module when a first ring gear and a second ring gear are fixed to each other according to an example embodiment.
Figure 25B:
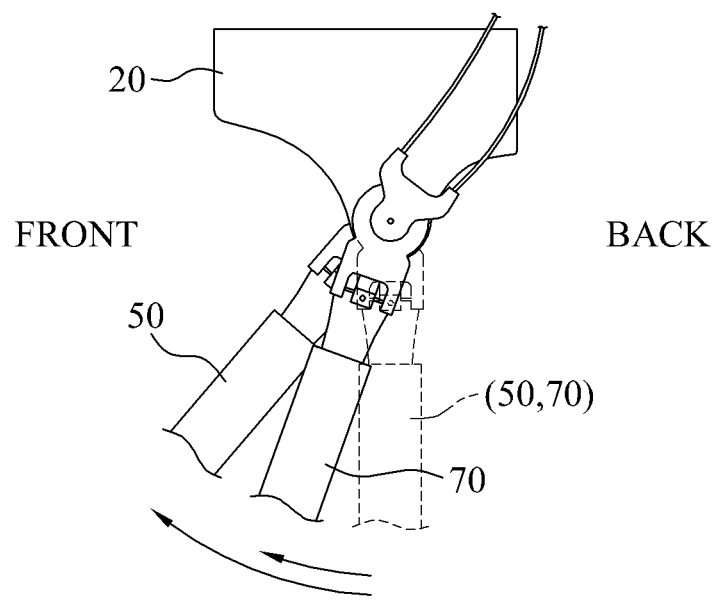

FIGS. 25A and 25B are views illustrating operations of the driving module 400, the first supporting module 50, and the second supporting module 70, as illustrated in FIG. 23, when the first ring gear 446 and the second ring gear 466 are fixed to each other according to an example embodiment. In particular, FIG. 25A illustrates operations of the first decelerator 440 and the second decelerator 460, and FIG. 25B illustrates operations of the first supporting module 50 and the second supporting module 70.

Although the first ring gear 446 and the second ring gear 466 may be provided in a non-fixed manner, a case in which the first ring gear 446 and the second ring gear 466 are provided in a fixed manner will be described first for ease of understanding.

Referring to FIG. 25A, when the sun gear 430 rotates counterclockwise, the first planet gear 442 and the second planet gear 462 may rotate clockwise. Further, the first planet gear 442 and the second planet gear 462 may revolve counterclockwise according to the counterclockwise rotation of the sun gear 430. Thus, the first carrier and the second carrier 464 may rotate counterclockwise.

When the number of teeth of the first ring gear 446 is smaller than the number of teeth of the second ring gear 466, a first gear ratio N1 may be smaller than a second gear ratio N2. Thus, the first carrier 444 may rotate at a faster angular velocity than the second carrier 464. The first carrier 444 and the second carrier 464 may have different angular velocities. Accordingly, the first pulley 448 and the second pulley 468 may have different angular velocities.

Thus, as shown in FIG. 25B, an angle between the first supporting module 50 and the second supporting module 70 may increase. The first supporting module 50 and the second supporting module 70 may move forward.

Conversely, when the sun gear 430 rotates clockwise, the first supporting module 50 and the second supporting module 70 may move backward.

In a state as shown in FIG. 25B, a user may apply a load for lifting an upper body of the user to the first decelerator 440 and the second decelerator 460 for upright walking. Hereinafter, descriptions will be provided with reference to FIGS. 26A and 26B.

Figure 26A:
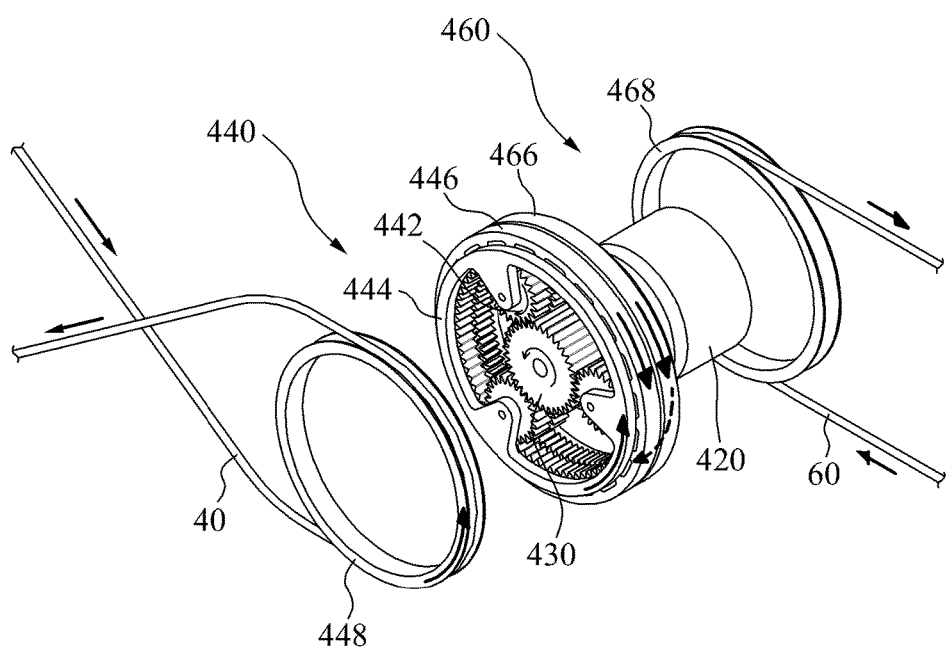
FIGS. 26A and 26B are views illustrating operations of a driving module, a first supporting module, and a second supporting module when power of a driving source is applied according to an example embodiment.
Figure 26B:
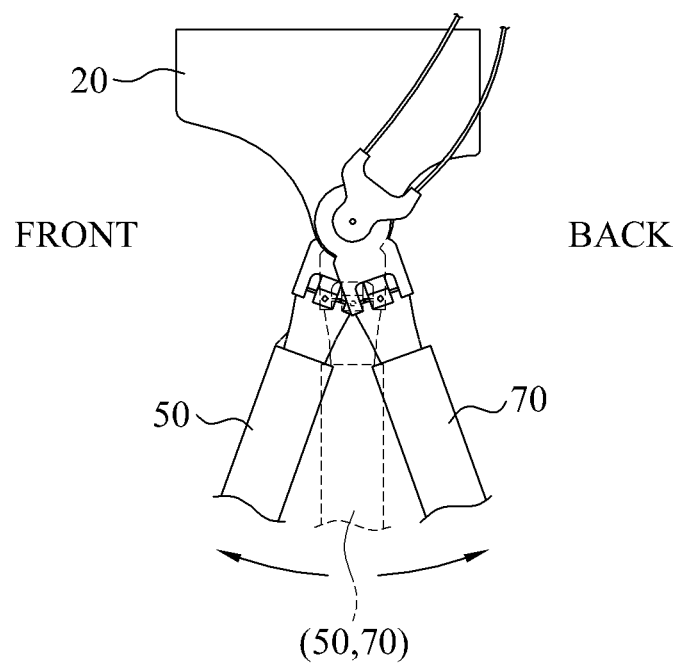

FIGS. 26A and 26B are views illustrating operations of the driving module 400, the first supporting module 50, and the second supporting module 70, as illustrated in FIG. 23, when power of the driving source 420 is applied according to an example embodiment. In particular, FIG. 26A illustrates operations of the first decelerator 440 and the second decelerator 460, and FIG. 26B illustrates operations of the first supporting module 50 and the second supporting module 70.

Referring to FIG. 26A, when a user applies a load for lifting an upper body of the user to the first decelerator 440 and the second decelerator 460 in a state in which power of the driving source 420 is applied, the first ring gear 446 and the second ring gear 466 may rotate.

When the user walks upright, the first ring gear 446 and the second ring gear 466 may rotate so that a rotation direction of the first carrier 444 may be opposite to a rotation direction of the second carrier 464. Thus, the first pulley 448 connected to the first carrier 444 and the second pulley 468 connected to the second carrier 464 may rotate in opposite directions.

Thus, when the sun gear 430 rotates counterclockwise, the first supporting module 50 may move forward, and the second supporting module 70 may move backward, as shown in FIG. 24B.

Conversely, when the sun gear 430 rotates clockwise, the first supporting module 50 may move backward, and the second supporting module 70 may move forward.

The controller 30 of FIG. 24 may alternately change a rotation direction of the sun gear 430, thereby assisting a walking motion of the user.

Figure 27A:
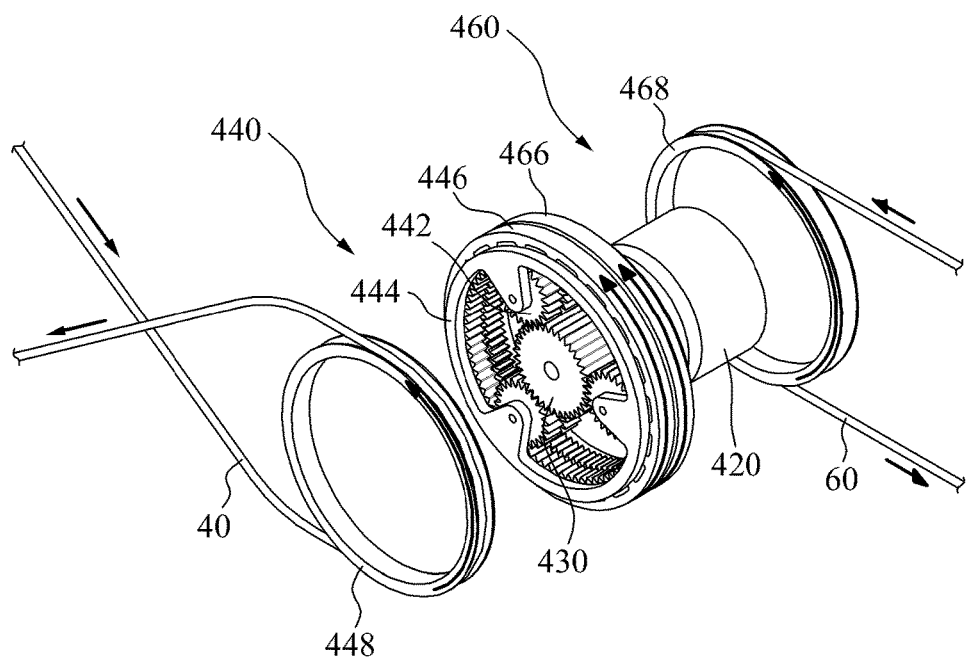
FIGS. 27A and 27B are views illustrating operations of a driving module, a first supporting module, and a second supporting module when power of a driving source is blocked according to an example embodiment.
Figure 27B:
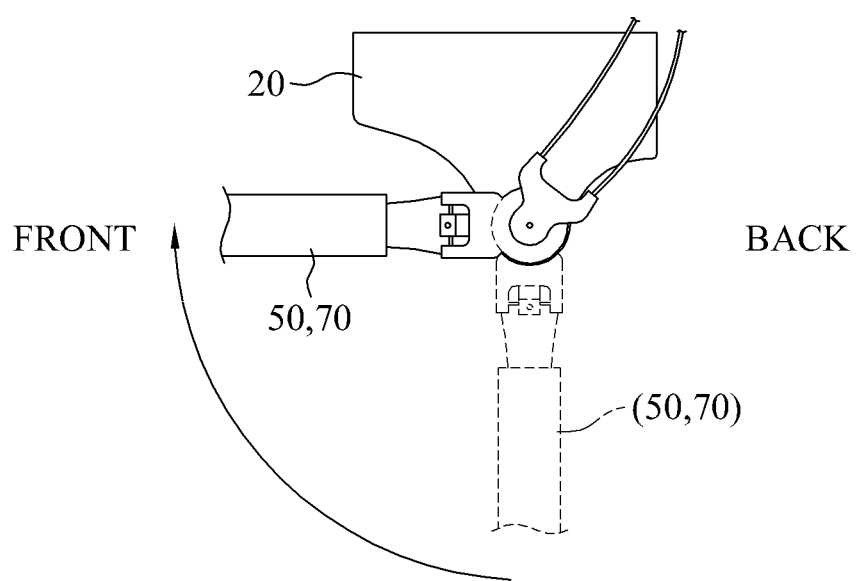

FIGS. 27A and 27B are views illustrating operations of the driving module 400, the first supporting module 50, and the second supporting module 70, as illustrated in FIG. 23, when power of the driving source 420 is blocked according to an example embodiment. In particular, FIG. 27A illustrates operations of the first decelerator 440 and the second decelerator 460, and FIG. 27B illustrates operations of the first supporting module 50 and the second supporting module 70.

Referring to FIG. 27A, when a user applies a load for bending an upper body of the user to the first decelerator 440 and the second decelerator 460 in a state in which the driving source 420 is powered off, the first supporting module 50 and the second supporting module 70 may transmit loads of identical directions to the first pulley 448 and the second pulley 468.

In this example, the first carrier 444, the second carrier 464, the first planet gear 442, the second planet gear 462, the first ring gear 446, the second ring gear 466, and the sun gear 430 may perform a single rigid body motion. The first carrier 444, the second carrier 464, the first planet gear 442, the second planet gear 462, the first ring gear 446, the second ring gear 466, and the sun gear 430 may have identical rotation velocities.

Thus, as shown in FIG. 27B, the user may freely perform a sitting-down motion without receiving the load by the driving source 420.

Conversely, when the user applies a load for lifting the upper body of the user to the first decelerator 440 and the second decelerator 460 in a state in which the driving source 420 is powered off, the user may freely perform a standing-up motion without receiving the load by the driving source 420.

The user may apply a load for bending the upper body of the user to the first decelerator 440 and the second decelerator 460 in a state in which the driving source 420 is held. For example, because the sun gear 430 is fixed, the first carrier 444 and the second carrier 464 may rotate at different angular velocities with respect to the sun gear 430. Further, as shown in FIG. 25B, the first supporting module 50 and the second supporting module 70 may move in identical directions to be spaced apart from each other. Through the foregoing process, the user may perform the sitting-down motion.

In this example, by enabling a ratio of a third gear ratio N3 between the first pulley 448 and the first joint assembly 42 to a fourth gear ratio N4 between the second pulley 468 and the second joint assembly 62 to be equal to an inverse number of a ratio of a first gear ratio N1 to a second gear ratio N2, the first supporting module 50 and the second supporting module 70 may be mitigated or prevented from being spaced apart from each other while the user is sitting down.

As another method, by reducing a difference between the first gear ratio N1 and the second gear ratio N2, an angle at which the first supporting module 50 and the second supporting module 70 are to be spaced apart from each other while the user is sitting down may be reduced. Thus, even when the difference between the first gear ratio N1 and the second gear ratio N2 is relatively small, the first supporting module 50 and the second supporting module 70 may secure an angular velocity sufficient for a walking motion using the driving source 420 having a high RPM value.

The three motion states described above may be arranged as shown in Table 4.

TABLE 4

| | Motion state | Driving source/Sun Gear |
|---|---|---|
| Walking | First supporting module forward/Second supporting module backward | ON/Clockwise |
| | First supporting module backward/Second supporting module forward | ON/Counterclockwise |
| | Sitting-down/Standing-up | (i) OFF/Not holding or not engaging the driving source |
| | | (ii) ON/Holding or engaging the driving source |

The controller 30 may include a processor and a memory (not shown). The controller 30 may be an arithmetic logic unit, a digital signal processor, a microcomputer, a field programmable array, a programmable logic unit, a microprocessor or any other device capable of responding to and executing instructions in a defined manner such that the controller 30 is programmed with instructions that configure the processing device as a special purpose computer and is configured to control at least the driving module 90 to transmit power to the first supporting module 50 and the second supporting module 70.

The instructions may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The program instructions may be executed by one or more processors.

Although a few example embodiments have been described, those skilled in the art will readily appreciate that many modifications are possible in the example embodiments without materially departing from the novel teachings and advantages of example embodiments. Accordingly, all such modifications are intended to be included within the scope of example embodiments as defined in the claims. For example, suitable results may be achieved if the described techniques are performed in a different order and/or if components in a described system, architecture, device, or circuit are combined in a different manner and/or replaced or supplemented by other components or their equivalents. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A driving module comprising:
    a driver configured to transmit power;
    an input side rotary body connected to the driver and configured to rotate; and
    a first decelerator and a second decelerator configured to operate using the power received from the driver through the input side rotary body, the first decelerator configured to transmit the power to a first supporting structure of a motion assistance apparatus, the second decelerator configured to transmit the power to a second supporting structure of the motion assistance apparatus,
    wherein a first gear ratio from the input side rotary body to a first output terminal of the first decelerator differs from a second gear ratio from the input side rotary body to a second output terminal of the second decelerator,
    wherein the first decelerator comprises a first planet gear, a first carrier, a first ring gear, and a first pulley,
    the second decelerator comprises a second planet gear, a second carrier, a second ring gear, and a second pulley,
    the first and second ring gears are fixed together to perform a single rigid body motion, and
    the first and second carriers are fixed to the first and second pulleys, respectively, to perform a single rigid body motion.

2. The driving module of claim 1, wherein
    at least one of the first planet gear or the second planet gear connected to an outer circumferential surface of the input side rotary body and configured to rotate with respect to an axis of rotation thereof and revolve around the input side rotary body using the power received through the input side rotary body,
    at least one of the first carrier or the second carrier connected to the axis of rotation of a corresponding one of the first planet gear or the second planet gear, and configured to rotate when the corresponding one of the first planet gear or the second planet gear revolves around the input side rotary body,
    at least one of the first ring gear or the second ring gear including an inner circumferential surface, the inner circumferential surface configured to be connected to a corresponding one of the first planet gear or the second planet gear, and
    at least one of the first pulley or the second pulley configured to act as a corresponding one of the first output terminal of the first decelerator or the second output terminal of the second decelerator, the at least one of the first pulley or the second pulley including an outer circumferential surface over which a power transmitter configured to transmit the power from the input side rotary body to a corresponding one of the first supporting structure or the second supporting structure that is connected to the driving module is to be wound.

3. The driving module of claim 2, wherein the first planet gear of the first decelerator and the second planet gear of the second decelerator are fixed together to perform a single rigid body motion.

4. The driving module of claim 2, wherein
    the first pulley and the first ring gear are fixed together to perform a single rigid body motion, or
    the second pulley and the second ring gear are fixed together to perform a single rigid body motion.

5. The driving module of claim 4, wherein
    the first pulley and the first ring gear are provided as an integral body such that the first pulley is defined along on a first outer circumferential surface of the first ring gear, or
    the second pulley and the second ring gear are provided as an integral body such
    that the second pulley is defined along on a second outer circumferential surface of the second ring gear.

6. The driving module of claim 4, wherein
    the first carrier is coupled to the axis of rotation of the first planet gear, and the first ring gear is restricted by the first planet gear and the first pulley, or the second carrier is coupled to the axis of rotation of the second planet gear,
    and the second ring gear is restricted by the second planet gear and the second pulley.

7. A motion assistance apparatus comprising:
    a fixing member configured to be fixed to a user;
    a driving module on one side of the fixing member, the driving module including,
        a driver configured to transmit power,
        an input side rotary body connected to the driver and configured to rotate,
        a first decelerator configured to operate based on the power received from the driver through the input side rotary body, the first decelerator configured to transmit the power to a first joint member of the motion assistance apparatus, and
        a second decelerator configured to operate based on the power received from the driver through the input side rotary body, the second decelerator configured to transmit the power to a second joint member of the motion assistance apparatus;
    the first joint member and the second joint member configured to assist respective rotary motions;
    a first power transmitter connected to a first output terminal of the first decelerator to the first joint member such that the first output terminal of the first decelerator and the first joint member are enabled to have opposite rotation directions; and a second power transmitter connected to a second output terminal of the second decelerator to the second joint member such that the second output terminal of the second decelerator and the second joint member are enabled to have identical rotation directions, wherein a first gear ratio from the input side rotary body to the first output terminal of the first decelerator differs from a second gear ratio from the input side rotary body to the second output terminal of the second decelerator, and wherein the first decelerator comprises a first planet gear, a first carrier, a first ring gear, and a first pulley, the second decelerator comprises a second planet gear, a second carrier, a second ring gear, and a second pulley, the first and second ring gears are fixed together to perform a single rigid body motion, and the first and second carriers are fixed to the first and second pulleys, respectively, to perform a single rigid body motion.

8. The motion assistance apparatus of claim 7, wherein the first power transmitter and the second power transmitter are asymmetrically provided to each other with respect to the driving module.

9. The motion assistance apparatus of claim 8, wherein when seeing from respective sides of the motion assistance apparatus, the first power transmitter is provided in an overlapping manner between the driving module and the first joint member, and the second power transmitter is provided in a non-overlapping manner between the driving module and the second joint member.

10. The motion assistance apparatus of claim 7, wherein the first pulley corresponds to the first output terminal of the first decelerator, and the second pulley corresponds to the second output terminal of the second decelerator.

11. A motion assistance apparatus comprising:
a fixing member configured to be fixed to a user;
a driving module on one side of the fixing member, the driving module including
a driver configured to transmit driving power,
an input side rotary body connected to the driver and configured to rotate,
a first decelerator configured to operate using the power received from the driver through the input side rotary body, the first decelerator configured to transmit the power to a first joint member of the motion assistance apparatus, and a second decelerator configured to operate using the power received from the driver through the input side rotary body, the second decelerator configured to transmit the power to a second joint member of the motion assistance apparatus;

the first joint member and the second joint member configured to assist respective rotary motions;

a first power transmitter connected to the first decelerator and the first joint member; and a second power transmitter connected to the second decelerator and the second joint member, and wherein a first gear ratio from the driver to a first output terminal of the first decelerator differs from a second gear ratio from the driver to a second output terminal of the second decelerator, the first decelerator comprises a first planet gear, a first carrier, a first ring gear, and a first pulley, the second decelerator comprises a second planet gear, a second carrier, a second ring gear, and a second pulley, the first and second ring gears are fixed together to perform a single rigid body motion, and the first and second carriers are fixed to the first and second pulleys, respectively, to perform a single rigid body motion.

12. The motion assistance apparatus of claim 11, wherein the first power transmitter is between the first output terminal of the first decelerator and the first joint member to enable the first output terminal of the first decelerator and the first joint member to have opposite rotation directions, and the second power transmitter is between the second output terminal of the second decelerator and the second joint member to enable the second output terminal of the second decelerator and the second joint member to have identical rotation directions.

13. The motion assistance apparatus of claim 12, wherein the first pulley corresponds to the first output terminal of the first decelerator, and the second pulley corresponds to the second output terminal of the second decelerator.

14. The motion assistance apparatus of claim 13, further comprising:
a first supporting module connected to the first joint member to support a first portion of the user; and
a second supporting module connected to the second joint member to support a second portion of the user.

15. The motion assistance apparatus of claim 14, wherein, when the driver is powered on, the first supporting module and the second supporting module are configured to rotate at different angular velocities such that the first supporting module and the second supporting module are either spaced apart from each other or to be close to each other.

* * * * *